(12) United States Patent
Mansouri

(10) Patent No.: US 9,707,177 B2
(45) Date of Patent: *Jul. 18, 2017

(54) DERMAL DELIVERY COMPOSITIONS COMPRISING ACTIVE AGENT-CALCIUM PHOSPHATE PARTICLE COMPLEXES AND METHODS OF USING THE SAME

(71) Applicant: Laboratory Skin Care, Inc., Tahoe City, CA (US)

(72) Inventor: Zahra Mansouri, Tahoe City, CA (US)

(73) Assignee: Laboratory Skin Care, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/259,010

(22) Filed: Apr. 22, 2014

(65) Prior Publication Data

US 2015/0004232 A1    Jan. 1, 2015

Related U.S. Application Data

(63) Continuation of application No. 13/858,677, filed on Apr. 8, 2013, now abandoned, which is a continuation of application No. 12/742,235, filed as application No. PCT/US2010/033942 on May 6, 2010, now Pat. No. 8,445,002.

(60) Provisional application No. 61/176,057, filed on May 6, 2009.

(51) Int. Cl.

| | |
|---|---|
| *A61K 9/00* | (2006.01) |
| *A61K 31/00* | (2006.01) |
| *A61K 9/16* | (2006.01) |
| *A61K 9/10* | (2006.01) |
| *A61K 31/353* | (2006.01) |
| *A61K 31/355* | (2006.01) |
| *A61K 31/525* | (2006.01) |
| *A61K 47/48* | (2006.01) |
| *A61K 9/14* | (2006.01) |
| *A61K 31/235* | (2006.01) |
| *A61K 31/60* | (2006.01) |
| *A61K 38/38* | (2006.01) |
| *A61K 38/40* | (2006.01) |

(52) U.S. Cl.
CPC .......... *A61K 9/1611* (2013.01); *A61K 9/0014* (2013.01); *A61K 9/10* (2013.01); *A61K 9/14* (2013.01); *A61K 9/1694* (2013.01); *A61K 31/235* (2013.01); *A61K 31/353* (2013.01); *A61K 31/355* (2013.01); *A61K 31/525* (2013.01); *A61K 31/60* (2013.01); *A61K 38/385* (2013.01); *A61K 38/40* (2013.01); *A61K 47/48853* (2013.01); *A61K 47/48861* (2013.01); *Y10T 428/2982* (2015.01)

(58) Field of Classification Search
CPC .. A61K 31/355; A61K 31/525; A61K 31/235; A61K 31/353; A61K 31/60; A61K 38/385; A61K 38/40; A61K 47/48853; A61K 47/48861; A61K 9/0014; A61K 9/10; A61K 9/14; A61K 9/1611; A61K 9/1694

See application file for complete search history.

(56) References Cited

U.S. PATENT DOCUMENTS

| | | | |
|---|---|---|---|
| 4,948,575 A | | 8/1990 | Cole et al. |
| 5,158,756 A | * | 10/1992 | Ogawa et al. ............... 423/309 |
| 5,604,200 A | | 2/1997 | Taylor-McCord |
| 6,096,324 A | | 8/2000 | Mansouri |
| 6,120,782 A | | 9/2000 | Mansouri |
| 6,262,020 B1 | | 7/2001 | Lezdey et al. |
| 6,395,311 B2 | * | 5/2002 | Jia ............................... 424/744 |
| 6,573,249 B2 | * | 6/2003 | Lezdey et al. ............... 514/54 |
| 7,651,694 B2 | * | 1/2010 | Lee ............................... 424/420 |
| 8,535,723 B2 | * | 9/2013 | Ogawa ................. A61K 9/0014 424/489 |
| 2002/0018797 A1 | | 2/2002 | Cui et al. |
| 2002/0068090 A1 | * | 6/2002 | Bell et al. ................... 424/491 |
| 2003/0134811 A1 | | 7/2003 | Jackson et al. |
| 2004/0180091 A1 | | 9/2004 | Lin |
| 2005/0013874 A1 | * | 1/2005 | Ito et al. ..................... 424/602 |
| 2005/0031699 A1 | | 2/2005 | Simonnet et al. |
| 2005/0234114 A1 | * | 10/2005 | Lee ............................. 514/365 |
| 2006/0039938 A1 | | 2/2006 | Josse |
| 2006/0257658 A1 | * | 11/2006 | Tanaka et al. ............... 428/402 |
| 2007/0003487 A1 | | 1/2007 | Ek |

(Continued)

FOREIGN PATENT DOCUMENTS

| | | |
|---|---|---|
| CN | 1813657 | 8/2006 |
| EP | 1514538 | 3/2005 |

(Continued)

OTHER PUBLICATIONS

Schmidt et al., Calcium phosphates in pharmaceutical tableting. 1. Physico-pharmaceutical properties, Pharm World Sci. Jun. 18, 1993;15(3):105-15, Abstract only.

(Continued)

*Primary Examiner* — Robert A Wax
*Assistant Examiner* — Olga V Tcherkasskaya
(74) *Attorney, Agent, or Firm* — Bret E. Field; Bozicevic, Field & Francis LLP

(57) ABSTRACT

Dermal delivery compositions are provided. Aspects of the dermal delivery compositions include the presence of active agent-calcium phosphate particle complexes, where these complexes include uniform, rigid, spherical nanoporous calcium phosphate particles associated with one or more active agents. Also provided are methods of using the compositions in active agent delivery applications.

12 Claims, 11 Drawing Sheets

(56) References Cited

U.S. PATENT DOCUMENTS

| | | |
|---|---|---|
| 2007/0166362 A1 | 7/2007 | Sakuma et al. |
| 2008/0051335 A1 | 2/2008 | Kleiner et al. |
| 2008/0160088 A1 | 7/2008 | Mackowiak |
| 2008/0220233 A1 | 9/2008 | Kjellin et al. |
| 2008/0241256 A1 | 10/2008 | Kuhn |
| 2009/0099651 A1 | 4/2009 | Hakimi-Mehr et al. |
| 2010/0086606 A1* | 4/2010 | Ogawa .................. A61K 9/0014 424/489 |
| 2012/0130435 A1 | 5/2012 | Hart et al. |
| 2012/0134919 A1 | 5/2012 | Engqvist et al. |
| 2012/0207803 A1 | 8/2012 | Bell |
| 2014/0199400 A1* | 7/2014 | Ogawa .................. A61K 9/0014 424/490 |

FOREIGN PATENT DOCUMENTS

| | | |
|---|---|---|
| EP | 1797900 | 6/2007 |
| FR | 2856593 A1 | 12/2004 |
| JP | 2008-291010 | 12/2008 |
| NO | WO2005025542 A1 | 3/2005 |
| WO | WO 00/15194 | 3/2000 |
| WO | WO 2005/084637 | 9/2005 |
| WO | WO2006038315 A1 | 4/2006 |
| WO | WO 2008/041846 | 4/2008 |
| WO | WO 2008101406 | 8/2008 |
| WO | WO 2010039560 | 4/2010 |

OTHER PUBLICATIONS

Carsetnsen et al., Physical and Chemical Properties of Calcium Phosphates for Solid State Pharmaceutical Formulations, Drug Development and Industrial Pharmacy, vol. 16, 1990—Issue 7, Abstract only.

Bohner, Calcium orthophosphates in medicine: from ceramics to calcium phosphate cements, Injury. Dec. 2000;31 Suppl 4:37-47, Abstract only.

* cited by examiner

|  | Skin Delivered Lysozyme (μg) | | Skin Delivered Lysozyme (%) | |
| --- | --- | --- | --- | --- |
| Tape layer | With Hydroxysomes™ | Without Hydroxysomes™ | With Hydroxysomes™ | Without Hydroxysomes™ |
| 1 | 7.210 μg | 48.35 μg | 0.60% | 4.03% |
| 2 | 0.979 μg | 0.56 μg | 0.08% | 0.047% |
| 3 | 0.284 μg | 0.03 μg | 0.02% | 0.002% |
| 4 | 0.100 μg | 0.00 μg | 0.01% | 0.00 |
| 5 | 0.029 μg | 0.00 μg | 0.002% | 0.00 |
| 6 | 0.024 μg | 0.00 μg | 0.002% | 0.00 | ns
DERMAL DELIVERY COMPOSITIONS COMPRISING ACTIVE AGENT-CALCIUM PHOSPHATE PARTICLE COMPLEXES AND METHODS OF USING THE SAME

CROSS-REFERENCE TO RELATED APPLICATIONS

This application is a continuation of U.S. application Ser. No. 13/858,677 filed Apr. 8, 2013; which application is a continuation of U.S. application Ser. No. 12/742,235 filed Apr. 12, 2011 and now issued as U.S.Pat. No. 8,445,002; which application claims benefit of the national stage entry of PCT/US2010/0333942 filed on May 6, 2010; which application, pursuant to 35 U.S.C. §119 (e), claims priority to the filing date of U.S. Provisional Patent Application Ser. No. 61/176,057 filed May 6, 2009; the disclosure of which applications are herein incorporated by reference.

INTRODUCTION

A variety of different active agents have been and continue to be developed for use in the treatment of a variety of different conditions, including both disease and non-disease conditions. For such applications, an effective amount of the active agent must be delivered to the subject in need thereof. A variety of different delivery formulations and routes have been developed, where such routes may vary depending on the nature of the active agent. Typically, less invasive delivery routes are better tolerated and therefore are more desirable.

One type of delivery route that is of great interest because of its minimally invasive nature is dermal delivery. In dermal delivery, an active agent composition is applied to a skin site to deliver the active agent to the subject. Many dermal delivery technologies currently in use or under evaluation are not entirely satisfactory. For example, certain dermal delivery technologies may disrupt the integrity of the stratum corneum (Sc) and/or rely on the presence of permeation enhancers, which can cause unwanted damage and/or irritation. In addition, certain dermal delivery technologies may be polymer- and/or liposome based technologies, neither of which technologies truly delivers through the Sc. Furthermore these technologies cannot be applied to large molecular weight bio-actives, etc.

As such, there continues to be a need for the development of new dermal delivery technologies which overcome one or more of the disadvantages experienced with current dermal delivery approaches.

SUMMARY

Dermal delivery compositions are provided. Aspects of the dermal delivery compositions include the presence of active agent-calcium phosphate particle complexes, where these complexes include uniform, rigid, spherical nanoporous calcium phosphate particles associated with one or more active agents. Also provided are methods of using the compositions in active agent delivery applications.

BRIEF DESCRIPTION OF THE FIGURES

FIG. 5A shows calcium phosphate particle penetration to the first layer of the stratum corneum. FIG. 5B shows calcium phosphate particle penetration to the third layer of the stratum corneum.

FIG. 10 is a table showing amount and percentage of lysozyme with and without calcium phosphate particles as measured by tape stripping.

DETAILED DESCRIPTION

Figure 1A:
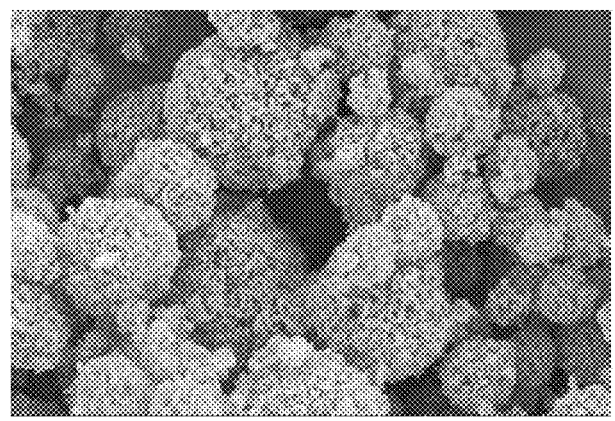
FIGS. 1A to 2B provide scanning electron microscope images of uniform, rigid, spherical, nanoporous calcium phosphate particles that find use in delivery compositions of the invention.

Dermal delivery compositions are provided. Aspects of the dermal delivery compositions include the presence of active agent-calcium phosphate particle complexes, where these complexes include uniform, rigid, spherical nanoporous calcium phosphate particles associated with one or more active agents. Also provided are methods of using the compositions in active agent delivery applications.

Before the present invention is further described, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In further describing various aspects of the invention, the active agent-calcium phosphate particles according to certain embodiments are described in greater detail, followed by a description of embodiments of delivery compositions that include the same, as well as methods of making and using the complexes and delivery compositions that include the same.

Delivery Compositions

As summarized above, active agent delivery compositions are provided. Active agent delivery compositions of the invention include active agent-calcium phosphate particle complexes present in a delivery vehicle. The active agent-calcium phosphate particle complex delivery vehicle components of the delivery compositions are now reviewed separately in greater detail.

Active Agent-Calcium Phosphate Particle Complexes

Active agent-calcium phosphate particle complexes that are present in delivery compositions of the invention include uniform, rigid, spherical, nanoporous calcium phosphate particles associated with one or more active agents. As the particles are associated with one or more active agents, one or more active agents are bound to the particles in some manner. The active agent(s) may be bound to the particles via a number of different associative formats, include but not limited to: ionic binding, covalent binding, Van der Waals interactions, hydrogen binding interactions, normal phase and reverse phase partition interactions, etc. As such, the particles may be described as being loaded with an amount of one or more active agents. By "loaded" is meant that the particles include an amount of one or more active agents (in other words an amount of a single active agent or two or more different active agents) that is bound to the particles. As the active agent is bound to the particles, the active agent does not dissociate from the particles in any substantial amount when the particles are present in the delivery composition. Because substantially none of the active agent dissociates from the particles, any amount that does dissociate is 30% or less, such as 20% or less, e.g., 10% or less, including 5% or less by weight of the originally bound amount of active agent. The amount of active agent component (which is made up of one or more distinct active agents) that is bound to the particles may vary depending on the particular active agent(s) making up the active agent bound particles, and in certain embodiments ranges from 0.01 to 1000 mg/g, such as from 0.1 to 750 mg/g and including 1 to 300 mg/g active agent(s)/gram particle.

The active agent is reversibly associated with the calcium phosphate particles. By "reversibly associated" is meant that the active agent is released from the calcium phosphate particles following delivery to a subject, e.g., following application a delivery composition that includes the complexes to a skin site. As reviewed in greater detail below, the calcium phosphate particles of the complexes degrade under acidic conditions, such as under conditions of pH 5 or less, e.g., pH 4.9 or less, pH 4.7 or less, pH 4.5 or less, pH 4.3 or less. When the particles degrade, they release their active agent "payload". The Stratum corneum (SC), the outer most layer of the skin, is made up roughly 20 layers of cells and is roughly 10 μm in thickness. The pH of the SC varies depending on its depth. Its outer most layers vary form pH 4.3 to 7.0, depending on the site sampled, or the individuals' sex. This pH rises to around 7.0 near the Stratum granulosum (SG). This rise is most dramatic in the last few layers of the SC adjoining the SG, as seen below. As such, as complexes of the invention penetrate into the SC, they degrade and concomitantly release any active agent associated therewith.

The released active agent retains its desired activity despite having been associated with the calcium phosphate particles in a complex. Accordingly, binding and release of the active agent to the calcium phosphate particles results in substantially little, if any, damage to the active agent. As such, the activity of the active agent is not diminished to an extent that adversely impacts its utility, where any reduction in activity caused by the association to the calcium phosphate particles that may occur with a given active agent is 10% or less, such as 5% or less and including 1% or less, e.g., as determined by an activity assay method, e.g., as described in the Experimental Section below.

In some embodiments, association of the active agent with the calcium phosphate particles in the complexes preserves one or more desirable features of the active agent, such as stability. In other words, the complex stabilizes the active agent, as compared to a control that lacks the calcium phosphate particles.

Uniform, Rigid, Spherical, Nanoporous Calcium Phosphate Particles

The calcium phosphate particles of the active agent-calcium phosphate particle complexes are uniform, rigid, spherical, nanoporous calcium phosphate particles. By "uniform" is meant that the shape of the particles does not vary substantially, such that the particles have substantially the same spherical shape. By "rigid" is meant that the particles are hard, such that they are not pliant. The term "spherical" is employed in its conventional sense to mean a round body whose surface is at all points substantially equidistant from the center. Of interest are calcium phosphate particles in which the median diameter is 20 μm or less, such as 10 μm or less, including 5 μm or less, where in some instances the medium diameter is 4 μm or less, such as 3 μm or less, including 2 μm or less. In a given calcium phosphate particulate composition, a distribution of diameters may be present, where in some instances the majority (such as 60% or more, 75% or more, 90% or more, 95% or more) of the particles have diameters that range from 0.01 to 20 µm, such as from 0.1 to 10 µm, and including from 0.1 to 2 µm. In some instances, the proportion of the particles that have an average particle diameter of 2 µm or less is 50% or more by number, such as 70% or more by number, including 90% or more by number.

The particles are nanoporous. By "nanoporous" is meant that the particles have a porosity of 30% or more, such as 40% or more, including 50% or more, where the porosity may range from 30% to 85%, such as from 40% to 70%, including from 45% to 55%, as determined using a mercury intrusion porosimeter porosity determination protocol as described in ASTM D 4284-88 "Standard Test Method for Determining Pore Volume Distribution of Catalysts by Mercury Intrusion Porosimetry". Porosity is also described by "pore volume (ml/g)" and in such instances many range from 0.1 ml/g to 2.0 ml/g. In some cases, the particles have a porosity such that their internal surface area ranges from 10 $m^2/g$ to 150 $m^2/g$, such as from 20 $m^2/g$ to 100 $m^2/g$, including 30 $m^2/g$ to 80 $m^2/g$, as determined using a BET gas adsorption surface area determination protocol as described in ASTM D3663-03 Standard Test Method for Surface Area of Catalysts and Catalyst Carriers. The pore diameter may vary, ranging in certain instances from 2 to 100 nm, such as 5 to 80 nm, including 10 to 60 nm. In addition, the particles may have a tapping density ranging from 0.2 $g/cm^3$ to 0.5 $g/cm^3$, such as from 0.25 $g/cm^3$ to 0.45 $g/cm^3$, including from 0.3 $g/cm^3$ to 0.4 $g/cm^3$. The tap density can be measured by using standard ASTM WK13023—New Determination of Tap Density of Metallic Powders by a Constant Volume Measuring Method.

The particles are, in some instances, chemically pure. By chemically pure is meant that the particles are made up of substantially one type of calcium phosphate mineral. In some instances, the calcium phosphate particles are described by the molecular formula $Ca_{10}(PO_4)_6(OH)_2$.

In some instances, the particles are ceramic particles. By ceramic is meant that the particles are produced using a method which includes a step of subjecting the particles to high temperature conditions, where such conditions are illustrated below. High temperatures may range from 200 to 1000° C., such as 300 to 900° C. and including 300 to 800° C. In some embodiments, the particles have a compression rupture strength ranging from 20 to 200 MPa, such as from 50 to 150 MPa, and including 75 to 90 MPa, as determined using a SHIMADZU MCT-W500 micro-compression testing machine particle strength determination protocol with a particle sintered at temperature of 400° C. to 900° C., as described in European Patent EP1840661.

In some embodiments, the particles are biodegradable, by which is meant that the particles degrade in some manner, e.g., dissolve, over time under physiological conditions. As the particles of these embodiments are biodegradeable under physiological conditions, they at least begin to dissolve at a detectable rate under conditions of pH of 5 or less, such as 4.5 or less, including 4.3 or less. As such, the particles exhibit solubility under acidic environments of pH 5 or less, such as upon application to the skin.

The calcium phosphate particles are non-toxic, e.g., as determined via US-FDA 21 CFR Part 58, non-mutagenic, e.g., as determined by Mutagenicity Ames Test, and non-irritating, e.g., as determined via Skin Sensitization RIPT (Human).

While the uniform, rigid, spherical, nanoporous calcium phosphate particles of the delivery compositions may vary in a variety of different parameters, including as reviewed above, in some embodiments the particles employed in the delivery compositions are chemically pure particles that have a mean diameter of 2 µm.

The uniform, rigid, spherical, nanoporous calcium phosphate particles of the delivery compositions of the invention may be prepared using any convenient protocol. Examples of fabrication protocols of interest include, but are not limited to, those described in U.S. Pat. Nos. 4,781,904; 5,039,408; 5,082,566; and 5,158,756; the disclosures of which are herein incorporated by reference. In one protocol of interest, the particles are manufactured by spray drying a slurry that includes nano calcium phosphate (e.g., hydroxyapatite) crystals (which may range from 2 nm to 100 nm size range) to produce uniform spherical nanoporous calcium phosphate particles. The resultant particles are then sintered for a period of time sufficient to provide mechanically and chemically stable rigid spheres. In this step, the sintering temperatures may range from 200° C. to 1000° C., such as 300° C. to 900° C. and including 300° C. to 800° C. for a period of time ranging from 1 hour to 10 hours, such as 2 hours to 8 hours and including 3 hours to 6 hours. Additional details regarding this method of manufacturing the uniform, rigid, spherical, nanoporous calcium phosphate particles are provided in U.S. Provisional Application Ser. No. 61/108, 805, the disclosure of which is herein incorporated by reference.

Active Agents

As summarized above, complexes of the invention include an active agent component (made of a single type of active agent or two or more different types of active agents) bound to the uniform, rigid, spherical, nanoporous calcium phosphate particles. The term "active agent" refers to any compound or mixture of compounds which produces a physiological result, e.g., a beneficial or useful result, upon contact with a living organism, e.g., a mammal, such as a human. Active agents are distinguishable from other components of the delivery compositions, such as carriers, diluents, lubricants, binders, colorants, etc. The active agent may be any molecule, as well as binding portion or fragment thereof, that is capable of modulating a biological process in a living subject. In certain embodiments, the active agent may be a substance used in the diagnosis, treatment, or prevention of a disease or as a component of a medication, cosmetic or cosmeceutical.

The active agent is a compound that interacts with or influences or otherwise modulates a target in a living subject. The target may be a number of different types of naturally occurring structures, where targets of interest include both intracellular and extra-cellular targets. The active agent may include one or more functional groups that provide for structural interaction with the intended target. Functional groups of interest include, but are not limited to: groups that participate in hydrogen bonding, hydrophobic-hydrophobic interactions, electrostatic interactions. Specific groups of interest include, but are not limited to amines, amides, sulfhydryls, carbonyls, hydroxyls, carboxyls, etc.

Active agents of interest may include cyclical carbon or heterocyclic structures and/or aromatic or polyaromatic structures substituted with one or more of the above functional groups. Also of interest as moieties of active agents are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The active agents may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the active agent may be obtained from a library of naturally occurring or synthetic molecules, including a library of compounds produced through combinatorial means, i.e., a compound diversity combinatorial library. When obtained from such libraries, the active agent employed will have demonstrated some desirable activity in an appropriate screening assay for the activity. Combinatorial libraries, as well as methods for producing and screening such libraries, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Active agents of interest include small, medium and large molecule active agents. Small molecule active agents are those active agents having a molecular weight ranging from 18 to 2500 daltons, such as 1000 to 1500 daltons and including 250 to 1000 daltons. Medium molecule active agents are those active agents having a molecular weight ranging from 2500 to 10,000 daltons, such as 4,000 to 8,000 daltons and including 5000 to 7000 daltons. Large molecule active agents are those active agents having a molecular weight of 10,000 daltons or more, such as 100,000 daltons or more, where in certain instances these large molecule active agents range from 1 million to 30 million daltons, such as 5 million to 20 million daltons and including 10 million to 15 million daltons.

In certain embodiments, the active agents are present in their salt forms, such that they carry a charge which allows them to bind to the uniform, rigid, spherical, nanoporous calcium phosphate particles of the delivery compositions in the desired manner.

Active agents of interest include, but are not limited to, those listed in Appendix A of U.S. Application Ser. No. 61/176,057; the disclosure of which is herein incorporated by reference.

Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; etc. Active agents of interest include, but are not limited to:

antibiotics, such as: aminoglycosides, e.g. amikacin, apramycin, arbekacin, bambermycins, butirosin, dibekacin, dihydrostreptomycin, fortimicin, gentamicin, isepamicin, kanamycin, micronomicin, neomycin, netilmicin, paromycin, ribostamycin, sisomicin, spectinomycin, streptomycin, tobramycin, trospectomycin; amphenicols, e.g. azidamfenicol, chloramphenicol, florfenicol, and theimaphenicol; ansamycins, e.g. rifamide, rifampin, rifamycin, rifapentine, rifaximin; b-lactams, e.g. carbacephems, carbapenems, cephalosporins, cehpamycins, monobactams, oxaphems, penicillins; lincosamides, e.g. clinamycin, lincomycin; macrolides, e.g. clarithromycin, dirthromycin, erythromycin, etc.; polypeptides, e.g. amphomycin, bacitracin, capreomycin, etc.; tetracyclines, e.g. apicycline, chlortetracycline, clomocycline, minocycline, etc.; synthetic antibacterial agents, such as 2,4-diaminopyrimidines, nitrofurans, quinolones and analogs thereof, sulfonamides, sulfones;

antifungal agents, such as: polyenes, e.g. amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g. butenafine, naftifine, terbinafine; imidazoles, e.g. bifonazole, butoconazole, chlordantoin, chlormidazole, etc., thiocarbamates, e.g. tolciclate, triazoles, e.g. fluconazole, itraconazole, terconazole;

anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

antimalarials, such as: acedapsone, amodiaquin, arteether, artemether, artemisinin, artesunate, atovaquone, bebeerine, berberine, chirata, chlorguanide, chloroquine, chlorproguanil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

antiprotozoan agents, such as: acranil, tinidazole, ipronidazole, ethylstibamine, pentamidine, acetarsone, aminitrozole, anisomycin, nifuratel, tinidazole, benzidazole, suramin;

cardioprotective agents, e.g., Zinecard (dexrazoxane); blood modifiers, including anticoagulants (e.g., coumadin (warfarin sodium), fragmin (dalteparin sodium), heparin, innohep (tinzaparin sodium), lovenox (enoxaparin sodium), orgaran (danaparoid sodium)) antiplatelet agents (e.g., aggrasta (tirofiban hydrochloride), aggrenox (aspirin/extended release dipyridamole), agrylin (anagrelide hydrochloride), ecotrin (acetylsalicylic acid), folan (epoprostenol sodium), halfprin (enteric coated aspirin), integrlilin (eptifibatide), persantine (dipyridamole USP), plavix (clopidogrel bisulfate), pletal (cilostazol), reopro (abciximab), ticlid (ticlopidine hydrochloride)), thrombolytic agents (activase (alteplase), retavase (reteplase), streptase (streptokinase)); adrenergic blockers, such as cardura (doxazosin mesylate), dibenzyline (phenoxybenzamine hydrochloride), hytrin (terazosin hydrochloride), minipress (prazosin hydrochloride), minizide (prazosin hydrochloride/polythiazide); adrenergic stimulants, such as aldoclor (methyldopa-chlorothiazide), aldomet (methyldopa, methyldopate HCl), aldoril (methyldopa-hydrochlorothiazide), catapres (clonidine hydrochloride USP, clonidine), clorpres (clonidine hydrochloride and chlorthalidone), combipres (clonidine hydrochloride/chlorthalidone), tenex (guanfacine hydrochloride); alpha/bet adrenergic blockers, such as coreg (carvedilol), normodyne (labetalol hydrochloride); angiotensin converting enzyme (ACE) inhibitors, such as accupril (quinapril hydrochloride), aceon (perindopril erbumine), altace (ramipril), captopril, lotensin (benazepril hydrochloride), mavik (trandolapril), monopril (fosinopril sodium tablets), prinivil (lisinopril), univasc (moexipril hydrochloride), vasotec (enalaprilat, enalapril maleate), zestril (lisinopril); angiotensin converting enzyme (ACE) inhibitors with calcium channel blockers, such as lexxel (enalapril maleate-felodipine ER); lotrel (amlodipine and benazepril hydrochloride), tarka (trandolapril/verapamil hydrochloride ER); angiotensin converting enzyme (ACE) inhibitors with diuretics, such as accuretic (quinapril HCl/hydroclorothiazide), lotensin (benazepril hydrochloride and hydrochlorothiazide USP), prinizide (lisinopri-hydrochlorothiazide), uniretic (moexipril hydrochloride/hydrochlorothiazide), vaseretic (enalapril maleate-hydrochlorothiazide), zestoretic (lisinopril and hydrochlorothiazide); angiotensin II receptor antagonists, such as atacand (candesartan cilexetil), avapro (irbesartan), cozaar (losartan potassium), diovan (valsartan), micardis (telmisartan), teveten (eprosartan mesylate); angiotensin II receptor antagonists with diuretics, such as avalide (irbesartan-hydrochlorothiazide), diovan (valsartan and hydrochlorothiazide), hyzaar (losartan potassium-hydrochlorothiazide); antiarrhythmics, such as Group I (e.g., mexitil (mexiletine hydrochloride, USP), norpace (disopyramide phosphate), procanbid (procainamide hydrochloride), quinaglute (quinidine gluconate), quinidex (quinidine sulfate), quinidine (quinidine gluconate injection, USP), rythmol (propafenone hydrochloride), tambocor (flecamide acetate), tonocard (tocamide HCl)), Group II (e.g., betapace (sotalol HCl), brevibloc (esmolol hydrochloride), inderal (propranolol hydrochloride), sectral (acebutolol hydrochloride)), Group III (e.g., betapace (sotalol HCl), cordarone (amiodarone hydrochloride), corvert (ibutilide fumarate injection), pacerone (amiodarone HCl), tikosyn (dofetilide)), Group IV (e.g., calan (verapamil hydrochloride), cardizem (diltiazem HCl), as well as adenocard (adenosine), lanoxicaps (digoxin), lanoxin (digoxin)); antilipemic acids, including bile acid sequestrants (e.g., colestid (micronized colestipol hydrochloride), welchol (colesevelam hydrochloride)), fibric acid derivatives (e.g., atromid (clofibrate), lopid (gemfibrozal tablets, USP), tricor (fenofibrate capsules)), HMG-CoA reductase inhibitors (e.g., baycol (cerivastatin sodium tablets), lescol (fluvastatin sodium), lipitor (atorvastatin calcium), mevacor (lovastatin), pravachol (pravastatin sodium), zocor (simvastatin)), Nicotinic Acid (e.g., Niaspan (niacin extended release tablets)); beta adrenergic blocking agents, e.g., betapace (sotalol HCl), blocadren (timolol maleate), brevibloc (esmolol hydrochloride), cartrol (carteolol hydrochloride), inderal (propranolol hydrochloride), kerlone (betaxolol hydrochloride), nadolol, sectral (acebutolol hydrochloride), tenormin (atenolol), toprol (metoprolol succinate), zebeta (bisoprolol fumarate); beta adrenergic blocking agents with diuretics, e.g., corzide (nadolol and bendroflumethiazide tablets), inderide (propranolol hydrochloride and hydroclorothiazide), tenoretic (atenolol and chlorthalidone), timolide (timolol maleate-hydrochlorothiazide), ziac (bisoprolol fumarate and hydrochlorothiazide); calcium channel blockers, e.g., adalat (nifedipine), calan (verapamil hydrochloride), cardene (nicardipine hydrochloride), cardizem (diltiazem HCl), covera (verapamil hydrochloride), isoptin (verapamil hydrochloride), nimotop (nimodipine), norvasc (amlodipine besylate), plendil (felodipine), procardia (nifedipine), sular (nisoldipine), tiazac (diltiazem hydrochloride), vascor (bepridil hydrochloride), verelan (verapamil hydrochloride); diuretics, including carbonic anhydrase inhibitors (e.g., daranide (dichlorphenamide)), combination diuretics (e.g., aldactazide (spironolactone with hydrochlorothiazide), dyazide (triamterene and hydrochlorothiazide), maxzide (triamterene and hydrochlorothiazide), moduretic (amiloride HCl-hydrochlorothiazide)), loop diuretics (demadex (torsemide), edecrin (ethacrynic acid, ethacrynate sodium), furosemide), potassium-sparing diuretics (aldactone (spironolactone), dyrenium (triamterene), midamor (amiloride HCl)), thiazides & related diuretics (e.g., diucardin (hydroflumethiazide), diuril (chlorothiazide, chlorothiazide sodium), enduron (methyclothiazide), hydrodiuril hydrochlorothiazide), indapamide, microzide (hydrochlorothiazide) mykrox (metolazone tablets), renese (polythi-azide), thalitone (chlorthalidone, USP), zaroxolyn (metolazone)); inotropic agents, e.g., digitek (digoxin), dobutrex (dobutamine), lanoxicaps (digoxin), lanoxin (digoxin), primacor (milrinone lactate); activase (alteplase recombinant); adrenaline chloride (epinephrine injection, USP); demser (metyrosine), inversine (mecamylamine HCl), reopro (abciximab), retavase (reteplase), streptase (streptokinase), tnkase (tenecteplase); vasodilators, including coronary vasodilators (e.g., imdur (isosorbide mononitrate), ismo (isosorbide mononitrate), isordil (isosorbide dinitrate), nitrodur (nitroglycerin), nitrolingual (nitroglycerin lingual spray), nitrostat (nitroglycerin tablets, USP), sorbitrate (isosorbide dinitrate)), peripheral vasodilators & combinations (e.g., corlopam (fenoldopam mesylate), fiolan (epoprostenol sodium), primacor (milrinone lactate)), vasopressors, e.g., aramine (metaramino) bitartrate), epipen (EpiPen 0.3 mg brand of epinephrine auto injector, EpiPen Jr. 0.15 mg brand of epinephrine auto injector), proamatine (midodrine hydrochloride); etc.

psychopharmacological agents, such as (1) central nervous system depressants, e.g. general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g. analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g. anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g. central antitussives (opium alkaloids and their derivatives);

pharmacodynamic agents, such as (1) peripheral nervous system drugs, e.g. local anesthetics (ester derivatives, amide derivatives), (2) drugs acting at synaptic or neuroeffector junctional sites, e.g. cholinergic agents, cholinergic blocking agents, neuromuscular blocking agents, adrenergic agents, antiadrenergic agents, (3) smooth muscle active drugs, e.g. spasmolytics (anticholinergics, musculotropic spasmolytics), vasodilators, smooth muscle stimulants, (4) histamines and antihistamines, e.g. histamine and derivative thereof (betazole), antihistamines (H1-antagonists, H2-antagonists), histamine metabolism drugs, (5) cardiovascular drugs, e.g. cardiotonics (plant extracts, butenolides, pentadienolids, alkaloids from erythrophleum species, ionophores,-adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g. antianemia drugs, blood coagulation drugs (hemostatics, anticoagulants, antithrombotics, thrombolytics, blood proteins and their fractions), (7) gastrointestinal tract drugs, e.g. digestants (stomachics, choleretics), antiulcer drugs, antidiarrheal agents, (8) locally acting drugs;

chemotherapeutic agents, such as (1) anti-infective agents, e.g. ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e. antineoplastic agents or cytotoxic drugs, such as alkylating agents, e.g. Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g. Vincristine (Oncovin), Vinblastine (Velban, Velbe), Paclitaxel (Taxol), and the like; antimetabolites, e.g. Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g. Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g. Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like.

Drug compounds of interest are also listed in: Goodman & Gilman's, The Pharmacological Basis of Therapeutics (9th Ed) (Goodman et al. eds) (McGraw-Hill) (1996); and 2001 Physician's Desk Reference.

Specific categories and examples of active agents include, but are not limited to: those appearing the following table:

| Therapeutic Category | Pharmacological Class | Structural Examples (Does not include derivatives) |
|---|---|---|
| Analgesics | Opioid Analgesics | Includes drugs such as Morphine, Meperidine and Propoxyphene |
| | Non-opioid Analgesics | Includes drugs such as Sodium Salicylate, Diflunisal, Para-Aminophenol Derivatives, Anthranilic Acid Derivatives, and Phenylpropionic Acid Derivatives |
| Anesthetics | | |
| Antibacterials | Beta-lactam, Cephalosporins | |
| | Beta-lactam, Penicillins | |
| | Beta-lactam, Other | Includes drugs such as Loracarbef |
| | Macrolides | |
| | Quinolones | |
| | Sulfonamides | |
| | Tetracyclines | |
| | Antibacterials, Other | Includes drugs such as Trimethoprim, Vancomycin, Lincomycin, Clindamycin, Furazolidone, Nitrofurantoin, Linezolid, Bacitracin, Chloramphenicol, Daptomycin, Fosfomycin, Methenamine, Metronidazole, Mupirocin, Rifaximin, Spectinomycin |
| Anticonvulsants | Calcium Channel Modifying Agents | Includes drugs such as Nifedipine |
| | Gamma-aminobutyric Acid (GABA) Augmenting Agents | Includes drugs such as Clonazepam, Diazepam, and Phenobarbital |
| | Glutamate Reducing Agents | |
| | Sodium Channel Inhibitors | |
| Antidementia Agents | Cholinesterase Inhibitors | |
| | Glutamate Pathway Modifiers | |
| | Antidementia Agents, Other | Includes drugs such as Ergoloid Mesylates |
| Antidepressants | Monoamino Oxidase (Type A) Inhibitors | |
| | Reuptake Inhibitors | |
| | Antidepressants, Other | Includes drugs such as Bupropion, Maprotiline, Mirtazapine, Trazodone |
| Antiemetics | | |
| Antifungals | | Includes drugs such as Amphotericin B, and Ketoconazole |
| Antigout Agents | | |

-continued

| Therapeutic Category | Pharmacological Class | Structural Examples (Does not include derivatives) |
|---|---|---|
| Anti-inflammatories | Glucocorticoids | See Adrenal Pharmacologic Class for similar/related therapies |
| | Nonsteroidal Anti-inflammatory Drugs (NSAIDs) | See Non-opioid Analgesics Pharmacologic Class for similar/related therapies |
| Antimigraine Agents | Abortive | See Analgesics Therapeutic Category for similar/related therapies |
| | Prophylactic | See Autonomic Agents and Cardiovascular Agents Therapeutic Categories for similar/related therapies |
| Antimycobacterials | Antituberculars | Includes drugs such as Isoniazid, Pyridoxine and Cycloserine |
| | Antimycobacterials, Other | Includes drugs such as Clofazimine, Dapsone, Rifabutin |
| Antineoplastics | Alkylating Agents | Includes drugs such as Chlorambucil, Thiotepa, Busulfan, Dacarbazine, and Carmustine |
| | Antimetabolites | Includes drugs such as Methotrexate, Cytarabine, and Mercaptopurine |
| | Immune Modulators and Vaccines | Includes biotech drugs as various Monoclonal Antibodies, Cytokines, Interferones and Interleukins |
| | Molecular Target Inhibitors | Includes drugs such as Vaccines, Antisense and Gene Therapies |
| | Nucleoside Analogues | Includes drugs such as dIdC, and AZT |
| | Protective Agents Topoisomerase Inhibitors | Includes biotech drugs as Vaccines |
| | Antineoplastics, Other | Includes drugs such as Carboplatin, Cisplatin, Oxaliplatin |
| Antiparasitics | Anthelmintics | Includes drugs such as Mebendazole, Pyrantel Pamoate, Bithionol, and Paromomycin |
| | Antiprotozoals | Includes drugs such as Chloroquine, Pyrimethamine, Metronidazole, Furazolidone, Melarsoprol, Suramin and Tetracyclines |
| | Pediculicides/Scabicides | Includes drugs such as Crotamiton, Lindane, Benzyl Benzoate and Sulfur |
| Antiparkinson Agents | Catechol O-methyltransferase (COMT) Inhibitors | |
| | Dopamine Agonists | Includes drugs such as Levodopa, and Deprenyl |
| | Antiparkinson Agents, Other | Includes drugs such as Benztropine, Biperidin, Bromocriptine, Diphenhydramine, Procyclidine, Selegiline, Trihexyphenidyl |
| Antipsychotics | Non-phenothiazines | Includes drugs such as Chlorprothixene, and Thiothixene |
| | Non-phenothiazines/Atypicals | Includes drugs such as Haloperidol, Molindone, and Loxapine |
| | Phenothiazines | Includes drugs such as Fluphenazine |
| Antivirals | Anti-cytomegalovirus (CMV) Agents | Includes biotech drugs as Vaccines |
| | Antiherpetic Agents | Includes biotech drugs as Vaccines and Recombinant Proteins |
| | Anti-human immunodeficiency virus (HIV) Agents, Fusion Inhibitors | |
| | Anti-HIV Agents, Non-nucleoside Reverse Transcriptase Inhibitors | |
| | Anti-HIV Agents, Nucleoside and Nucleotide Reverse Transcriptase Inhibitors | |
| | Anti-HIV Agents, Protease Inhibitors | |
| | Anti-influenza Agents | Includes biotech drugs such as Vaccines, Flumist, and Thymidine Kinase Inhibitors |
| | Antivirals, Other | Includes drugs such as Adefovir and Ribavirin |
| Anxiolytics | Antidepressants | |
| | Anxiolytics, Other | Includes drugs such as Buspirone and Meprobamate |
| Autonomic Agents | Parasympatholytics | |
| | Parasympathomimetics | |
| | Sympatholytics | See Cardiovascular Agents and Genitourinary Agents Therapeutic Categories for similar/related therapies |
| | Sympathomimetics | See Cardiovascular Agents Therapeutic Category for similar/related therapies |
| Bipolar Agents | | |
| Blood Glucose Regulators | Antihypoglycemics | |
| | Hypoglycemics, Oral Insulins | |
| Blood Products/Modifiers/Volume Expanders | Anticoagulants | Includes drugs such as Acetaminophen, Coumarin Derivatives, Aspirin, Heparin, and Indandione Derivatives |
| | Blood Formation Products Coagulants Platelet Aggregation Inhibitors | |

-continued

| Therapeutic Category | Pharmacological Class | Structural Examples (Does not include derivatives) |
|---|---|---|
| Cardiovascular Agents | Alpha-adrenergic Agonists | See Autonomic Agents Therapeutic Category for similar/related therapies |
| | Alpha-adrenergic Blocking Agents | Includes drugs such as Phenolamine Mesylate, and Prazosin HCl |
| | Antiarrhythmics | Includes drugs such as Bretylium, Digitalis, Quinidine, and Atropine |
| | Beta-adrenergic Blocking Agents | Includes drugs such as Atenolol and related compounds |
| | Calcium Channel Blocking Agents | Includes drugs such as Nifedipine |
| | Direct Cardiac Inotropics | |
| | Diuretics | Includes drugs such as Furosemide, and Spironolactone |
| | Dyslipidemics | |
| | Renin-angiotensin-aldosterone System Inhibitors | Includes drugs such as Captopril, and Saralasin Acetate |
| | Vasodilators | Includes drugs such as Sodium Nitroprusside, Nitroglycerine |
| Central Nervous System Agents | Amphetamines | |
| | Non-amphetamines | |
| Dental and Oral Agents | | Includes such drugs as CHG |
| Dermatological Agents | Dermatological Anesthetics | Includes drugs such as Lidocaine, Dibucaine, and Diperodon |
| | Dermatological Antibacterials | Includes drugs such as Bacitracin, Chlorotetracycline, and Erythromycin |
| | Dermatological Antifungals | Includes drugs such as Haloprogin, Tolnaftate, Imidazoles, and Polyene Antibiotics |
| | Dermatological Anti-inflammatories | Includes drugs such as Hydrocortisone, Amcinonide, and Desonide |
| | Dermatological Antipruritic Agents | Includes drugs such as Benzocaine, Lidocaine, Pramoxine, Diphenhydramine, and Hydrocortisone |
| | Dermatological Antivirals | HIV-Inhibitors of reverse transcriptase (Nucleoside analogs, Non-nucleoside analogs, and Nucleotide analogs), Viral packaging inhibitors (Protease Inhibitors), Fusion Inhibitors, Herpes Virus-Nucleoside analogs (Acyclovir, Valacyclovir, Famciclovir and Penciclovir), Interferone Alpha, and Imiquimod |
| | Dermatological Keratolytics | Includes drugs such as Urea, and Salicylic Acid |
| | Dermatological Mitotic Inhibitors | Includes drugs such as Vinblastine, and Vincristine |
| | Dermatological Photochemotherapy Agents | Includes drugs such as Hydroquinone and Trioxsalen |
| | Dermatological Retinoids | Includes drugs such as Tretinoin |
| | Dermatological Tar Derivatives | Includes drugs such as Anthraquinone derivatives (Anthralin) |
| | Dermatological Vitamin D Analogs | Includes drugs such as Calcitriol, and Calcipotriol |
| | Dermatological Wound Care Agents | Includes drugs such as Collagenase, Sutilains and Dextranomers |
| | Dermatological Antiacne | Includes drugs such as Benzoyl Peroxide, and Salicylic Acid |
| | Dermatological UVA/UVB Block | Includes actives such as 3_Benzylidene_Camphors, 2-phenylbenzimidazole-5-sulfonic acid, Octyl Salicylate, Homosalate, Octylmethyl PABA, , Octyl Methoxycinnamate, Octocrylene, Oxybenzone, Menthyl Anthranilate, Titanium Dioxide, Zinc Oxide, Avobenzone |
| Deterrents/ Replacements | Alcohol Deterrents | |
| Enzyme Replacements/ Modifiers | | |
| Gastrointestinal Agents | Antispasmodics, Gastrointestinal | |
| | Histamine2 (H2) Blocking Agents | Includes drugs such as Cimetidine, and Ranitidine |
| | Irritable Bowel Syndrome Agents | |
| | Protectants | |
| | Proton Pump Inhibitors | |
| | Gastrointestinal Agents, Other | Includes drugs such as Sevelamer, Ursodiol, Antisense, Vaccines and Mab and their fragments |

-continued

| Therapeutic Category | Pharmacological Class | Structural Examples (Does not include derivatives) |
|---|---|---|
| Genitourinary Agents | Antispasmodics, Urinary | |
| | Benign Prostatic Hypertrophy Agents | See Autonomic Agents and Cardiovascular Agents Therapeutic Categories for similar/related therapies |
| | Impotence Agents | |
| | Prostaglandins | See Hormonal Agents, Stimulant/Replacement/Modifying TherapeuticCategory for similar/related therapies |
| Hormonal Agents, Stimulant/ Replacement/ Modifying | Adrenal | See Anti-inflammatories Therapeutic Category for similar/related therapies |
| | Parathyroid/Metabolic Bone Disease Agents | |
| | Pituitary | |
| | Prostaglandins | See Genitourinary Agents Therapeutic Category for similar/related therapies |
| | Sex Hormones/Modifiers | |
| | Thyroid | Includes drugs such as Levothyroxine Sodium, and Methimazoie |
| Hormonal Agents, Suppressant | Adrenal | |
| | Pituitary | Includes biotech drugs as hGH |
| | Sex Hormones/Modifiers | Includes biotech drugs as Estradiol |
| | Thyroid | |
| Immunological Agents | Immune Stimulants | Includes biotech drugs as various Monoclonal Antibodies, Interferones and Interleukins |
| | Immune Suppressants | Includes biotech drugs as various Monoclonal Antibodies, Interferones and Interleukins |
| | Immunomodulators | Includes biotech drugs as various Monoclonal Antibodies, Interferones and Interleukins |
| Inflammatory Bowel Disease Agents | Glucocorticoids | See Hormonal Agents, Stimulant/Replacement/Modifying Therapeutic Category for similar/related therapies |
| | Salicylates | |
| | Sulfonamides | See Antibacterial Therapeutic Category for similar/related therapies |
| Ophthalmic Agents | Ophthalmic Anti-allergy Agents | Includes drugs such as Cromolyn |
| | Ophthalmic Antibacterials | Includes drugs such as Bacitracin, Chloramphenicol, Erythromycin, and Polymyxin B Sulfate |
| | Ophthalmic Antifungals | Includes drugs such as Amphotericm B, Miconazole, Natamycin and Nystatin |
| | Ophthalmic Antiglaucoma Agents | Includes drugs such as Pilocarpine HCl, Carbachol, Physostigmine Salicylate, Isoflurophate, and Acetazolamide |
| | Ophthalmic Anti-inflammatories | Includes drugs such as Hydrocortisone, Dexamethasone, and Medrysone |
| | Ophthalmic Antivirals | Includes drugs such as Idoxuridine, Trifluridine, Antisense, and Vidarabine |
| | Ophthalmics, Other | Includes drugs such as Formivirsen |
| Otic Agents | Otic Antibacterials | Includes drugs such as Chloramphenicol, Neomycin Sulfate, and Polymyxins |
| | Otic Anti-inflammatories | |
| Respiratory Tract Agents | Antihistamines | |
| | Antileukotrienes | |
| | Bronchodilators, Anticholinergic | |
| | Bronchodilators, Anti-inflammatories | Includes drugs such as Corticosteroid derivatives |
| | Bronchodilators, Phosphodiesterase 2 Inhibitors (Xanthines) | |
| | Bronchodilators, Sympathomimetic | Includes drugs such as Albuterol, Terbutaline, and Isoproterenol |
| | Mast Cell Stabilizers | Includes drugs such as Cromolyn Sodium |
| | Mucolytics | |
| | Respiratory Tract Agents, Other | Includes drugs such as Alpha-1-proteinase Inhibitor, Human; Benzonatate; Guaifenesin; Iodinated Glycerol; Potassium Iodide; Tetrahydrozoline |

| Therapeutic Category | Pharmacological Class | Structural Examples (Does not include derivatives) |
|---|---|---|
| Sedatives/ Hypnotics | | |
| Skeletal Muscle Relaxants | | Includes drugs such as Carisoprodol, Chlorphenesin Carbamate, Chlorzoxazone, and Cyclobenzaprine HCl |
| Therapeutic Nutrients/ Minerals/Electrolytes | Electrolytes/Minerals | |
| | Vitamins | |
| Toxicologic Agents | Opioid Antagonists | |
| Erectial dysfunction Agents | | Tadalafil, sildenafil, vardenafil |

Specific compounds of interest also include, but are not limited to:

Hydrocodone/Acetaminophen
Azithromycin
Simvastatin
Oxycodone ER
Sertraline
Fentanyl Transdermal
Amlodipine Besylate
Fexofenadine
Amoxicillin/Pot Clav
Omeprazole
Gabapentin
Fluticasone Nasal
Lisinopril
Oxycodone w/Acetaminophen
Metoprolol Succinate
Metformin
NovoLog
Amlodipine Besylate
Levothyroxine
Zolpidem Tartrate
Amoxicillin
Ondansetron
Paroxetine
Alprazolam
Lovastatin
Albuterol Aerosol
Fluoxetine
Lorazepam
Warfarin
Pravastatin
Cefdinir
Atenolol
Hydrochlorothiazide
Tramadol
Clonazepam
Cephalexin
Bupropion SR
Oxycodone
Propoxyphene-N/Acetaminophen
Lisinopril/Hydrochlorothiazide
Finasteride
Citalopram HBr
Nifedipine ER
Cyclobenzaprine
Furosemide Oral
Carisoprodol
Morphine Sulfate ER
Ciprofloxacin HCl
Metoprolol Tartrate
Prednisone Oral
Cartia XT
Amphetamine Salt Cmb
Clindamycin Systemic
Nabumetone
Potassium Chloride
Ondansetron ODT Lipitor
Nexium
Advair Diskus
Prevacid
Plavix
Singulair
Seroquel
Effexor XR
Lexapro
Actos
Protonix
Vytorin
Topamax
Risperdal
Abilify
Cymbalta
Lamictal
Zyprexa
Levaquin
Celebrex
Zetia
Valtrex
Crestor
Fosamax
Zyrtec
Lantus
Adderall XR
Diovan
Avandia
Tricor
Aciphex
Diovan HCT
OxyContin
Concerta
Coreg
Flomax
Lyrica
Wellbutrin XL
Aricept
Imitrex Oral
Ambien
Lotrel
Nasonex
Toprol XL
Ambien CR
Enbrel
Spiriva
Viagra
Lidoderm
Actonel
Chantix
Norvasc
Lovenox
Provigil
Lunesta
Altace Diltiazem CD
Verapamil SR
Albuterol Nebulizer Solution
Felodipine ER
Quinapril
Clopidogrel
Ibuprofen
Ranitidine HCl
Glyburide/Metformin HCl
Minocycline
Triamterene w/Hydrochlorothiazide
Enalapril
Oxybutynin Chl ER
Tramadol HCl/Acetaminophen
Meloxicam
Acetaminophen w/Codeine
Spironolactone
Hydroxyzine
Naproxen
Glipizide ER
Trazodone HCl
Fluconazole
Mirtazapine
Promethazine Tabs
Phentermine
Glyburide
Tizanidine HCl
Diazepam
Venlafaxine
Metformin HCl ER
Buspirone HCl
Diclofenac Sodium
Doxycycline
Gemfibrozil
Cefprozil
Propranolol HCl
Phenytoin Sodium Ext
Isosorbide Mononitrate
Clarithromycin
Clozapine
Vancocin HCl
Glimepiride
Clotrimazole/Betamethasone
Carbidopa/Levodopa
Mupirocin
Desmopressin Acetate
Nitrofurantoin Monohydrate
Clonidine
Clarithromycin ER
Trimethoprim Sulfate
Nifedical XL
Carvedilol
Methotrexate
Hydrocodone/Ibuprofen
Methylprednisolone Tabs
Etodolac
Nifedipine
Bupropion ER Keppra
Geodon Oral
Cozaar
Detrol LA
Atripla
Truvada
CellCept
Pulmicort Respules
Humalog
Depakote ER
Depakote
Premarin Tabs
Synthroid
Niaspan
Byetta
Budeprion XL
Strattera
Combivent
Trileptal
Yasmin 28
Flovent HFA
Skelaxin
Prograf
Arimidex
Evista
Hyzaar
Namenda
Januvia
Humira
Cialis
Reyataz
Xalatan
Omnicef
Avelox
ProAir HFA
Asacol
Benicar HCT
Fentanyl Oral Citra
Requip
Boniva
Caduet
Avapro
Gleevec
Kaletra
Ortho TriCyclen Lo
Benicar
AndroGel
Xopenex
Procrit
Lamisil Oral
Avalide
Nasacort AQ
Combivir
Allegra-D 12 Hour
Duragesic
Copaxone
RenaGel
Femara

| | |
|---|---|
| Nystatin Systemic | Enbrel Sureclick |
| Benazepril | NovoLog Mix 70/30 |
| Zegerid | Clarinex |
| Cefuroxime Axetil | Aldara |
| Amitriptyline | Forteo |
| Bupropion XL | Suboxone |
| Clobetasol | Avodart |
| Acyclovir | Paxil CR |
| Benzonatate | Norvir |
| Allopurinol | Avandamet |
| Penicillin VK | Restasis |
| Temazepam | Avonex |
| Baclofen | Sensipar |
| Tretinoin | Tarceva |
| Sulfamethoxazole/Tri | Patanol |
| Terbinafine HCL | Yaz |
| Methadone HCl Non-Injection | Lovaza |
| Amiodarone | Mirapex |
| Ketoconazole Topical | Focalin XR |
| Hydroxy-chloroquine | Cosopt |
| Nitrofurantoin Macrocrystals | Zyvox |
| Triamcinolone Acetonide Top | Epzicom |
| Lithium Carbonate | NuvaRing |
| Terazosin | Actiq |
| Itraconazole | Foxamax Plus D |
| Hydralazine | Actoplus Met |
| Butalbital/Acetaminophen/Caffeine | Lumigan |
| Labetalol | Rhinocort Aqua |
| Fosinopril Sodium | Solodyn |
| Cilostazol | Thalomid |
| Mometasone Topical | Fuzeon |
| Doxazosin | Astelin |
| Clindamycin Topical | BenzaClin |
| Metoclopramide | Relpax |
| Medroxyprogesterone Injection | Viread |
| Megestrol Oral Suspension | Casodex |
| Folic Acid | Vigamox |
| Zostavax | Vesicare |
| Nitroglycerin | Humalog Mix 75/25 Pn |
| Bisoprolol/Hydrochlorothiazide | Trizivir |
| Polyethylene Glycol | Budeprion SR |
| Prednisolone Sd Phosphate Oral | Xeloda |
| Azathioprine | Sustiva |
| Calcitriol | Levitra |
| Torsemide | Endocet |
| Glipizide | Risperdal Consta |
| Sotalol | Aggrenox |
| Zonisamide | Humira Pen |
| Hydromorphone HCl | Kadian |
| Potassium Chloride | Differin |
| Oxcarbazepine | Catapres-TTS |
| Diltiazem SR | Alphagan P |
| Albuterol Sulfate/Ipratropium | Tussionex |
| Metronidazole Tabs | Zyrtec Syrup |
| Cabergoline | Maxalt |
| Cyclosporine | Zoloft |
| Estradiol Oral | Prilosec |
| Methocarbamol | Ciprodex Otic |
| Tamoxifen | Temodar |
| Promethazine/Codeine | TobraDex |
| Ursodiol | Zyrtec-D |
| Mercaptopurine | Welchol |
| Ribavirin | Maxalt MLT |
| Famotidine | Asmanex |
| PhosLo | Atacand |
| Indomethacin SR | Coumadin Tabs |
| Lamotrigine | Dovonex |
| Cefadroxil | Klor-Con |
| Ipratropium Br Nebulizer Solution | Pegasys |
| Fluvoxamine | Ultram ER |
| Methylphenidate | Betaseron |
| Metolazone | Zovirax Topical |
| Microgestin Fe 1/20 | Trinessa |
| Dexamphetamine Sulfate | Pulmozyme |
| Diltiazem ER | Neupogen |
| Clindesse | Humulin N |
| Flecainide Acetate | Micardis HCT |
| Metronidazole Top | Ortho Evra |
| Microgestin Fe 1/20 | Allegra-D 12 Hours |
| Evoclin | Fentora |
| Primidone | Enablex |
| Fluocinonide | Famvir |
| Terconazole | Avinza |
| Carbidopa/Levodopa ER | Prempro |
| Leflunomide | Coreg CR |
| Midodrine HCl | Marinol |

Specific compounds of interest also include, but are not limited to:

antineoplastic agents, as disclosed in U.S. Pat. Nos. 5,880,161, 5,877,206, 5,786,344, 5,760,041, 5,753,668, 5,698,529, 5,684,004, 5,665,715, 5,654,484, 5,624,924, 5,618,813, 5,610,292, 5,597,831, 5,530,026, 5,525,633, 5,525,606, 5,512,678, 5,508,277, 5,463,181, 5,409,893, 5,358,952, 5,318,965, 5,223,503, 5,214,068, 5,196,424, 5,109,024, 5,106,996, 5,101,072, 5,077,404, 5,071,848, 5,066,493, 5,019,390, 4,996,229, 4,996,206, 4,970,318, 4,968,800, 4,962,114, 4,927,828, 4,892,887, 4,889,859, 4,886,790, 4,882,334, 4,882,333, 4,871,746, 4,863,955, 4,849,563, 4,845,216, 4,833,145, 4,824,955, 4,785,085, 476925, 4,684,747, 4,618,685, 4,611,066, 4,550,187, 4,550, 186, 4,544,501, 4,541,956, 4,532,327, 4,490,540, 4,399,283, 4,391,982, 4,383,994, 4,294,763, 4,283,394, 4,246,411, 4,214,089, 4,150,231, 4,147,798, 4,056,673, 4,029,661, 4,012,448;

psycopharmacological/psychotropic agents, as disclosed in U.S. Pat. Nos. 5,192,799, 5,036,070, 4,778,800, 4,753, 951, 4,590,180, 4,690,930, 4,645,773, 4,427,694, 4,424,202, 4,440,781, 5,686,482, 5,478,828, 5,461,062, 5,387,593, 5,387,586, 5,256,664, 5,192,799, 5,120,733, 5,036,070, 4,977,167, 4,904,663, 4,788,188, 4,778,800, 4,753,951, 4,690,930, 4,645,773, 4,631,285, 4,617,314, 4,613,600, 4,590,180, 4,560,684, 4,548,938, 4,529,727, 4,459,306, 4,443,451, 4,440,781, 4,427,694, 4,424,202, 4,397,853, 4,358,451, 4,324,787, 4,314,081, 4,313,896, 4,294,828, 4,277,476, 4,267,328, 4,264,499, 4,231,930, 4,194,009, 4,188,388, 4,148,796, 4,128,717, 4,062,858, 4,031,226, 4,020,072, 4,018,895, 4,018,779, 4,013,672, 3,994,898, 3,968,125, 3,939,152, 3,928,356, 3,880,834, 3,668,210;

cardiovascular agents, as disclosed in U.S. Pat. Nos. 4,966,967, 5,661,129, 5,552,411, 5,332,737, 5,389,675, 5,198,449, 5,079,247, 4,966,967, 4,874,760, 4,954,526, 5,051,423, 4,888,335, 4,853,391, 4,906,634, 4,775,757, 4,727,072, 4,542,160, 4,522,949, 4,524,151, 4,525,479, 4,474,804, 4,520,026, 4,520,026, 5,869,478, 5,859,239, 5,837,702, 5,807,889, 5,731,322, 5,726,171, 5,723,457, 5,705,523, 5,696,111, 5,691,332, 5,679,672, 5,661,129, 5,654,294, 5,646,276, 5,637,586, 5,631,251, 5,612,370, 5,612,323, 5,574,037, 5,563,170, 5,552,411, 5,552,397, 5,547,966, 5,482,925, 5,457,118, 5,414,017, 5,414,013, 5,401,758, 5,393,771, 5,362,902, 5,332,737, 5,310,731, 5,260,444, 5,223,516, 5,217,958, 5,208,245, 5,202,330, 5,198,449, 5,189,036, 5,185,362, 5,140,031, 5,128,349, 5,116,861, 5,079,247, 5,070,099, 5,061,813, 5,055,466, 5,051,423, 5,036,065, 5,026,712, 5,011,931, 5,006,542, 4,981,843, 4,977,144, 4,971,984, 4,966,967, 4,959,383, 4,954,526, 4,952,692, 4,939,137, 4,906,634, 4,889,866, 4,888,335, 4,883,872, 4,883,811, 4,847,379, 4,835,157, 4,824,831, 4,780,538, 4,775,757, 4,774,239, 4,771,047, 4,769,371, 4,767,756, 4,762,837, 4,753,946, 4,752,616, 4,749,715, 4,738,978, 4,735,962, 4,734,426, 4,734,425, 4,734,424, 4,730,052, 4,727,072, 4,721,796, 4,707,550, 4,704,382, 4,703,120, 4,681,970, 4,681,882, 4,670,560, 4,670,453, 4,668,787, 4,663,337, 4,663,336, 4,661,506, 4,656,267, 4,656,185, 4,654,357, 4,654,356, 4,654,355, 4,654,335, 4,652,578, 4,652,576, 4,650,874, 4,650,797, 4,649,139, 4,647,585, 4,647,573, 4,647,565, 4,647,561, 4,645,836, 4,639,461, 4,638,012, 4,638,011, 4,632,931, 4,631,283, 4,628,095, 4,626,548, 4,614,825, 4,611,007, 4,611,006, 4,611,005, 4,609,671, 4,608,386, 4,607,049, 4,607,048, 4,595,692, 4,593,042, 4,593,029, 4,591,603, 4,588,743, 4,588,742, 4,588,741, 4,582,854, 4,575,512, 4,568,762, 4,560,698, 4,556,739, 4,556,675, 4,555,571, 4,555,570, 4,555,523, 4,550,120, 4,542,160, 4,542,157, 4,542,156, 4,542,155, 4,542,151, 4,537,981, 4,537,904, 4,536,514, 4,536,513, 4,533,673, 4,526,901, 4,526,900, 4,525,479, 4,524,151, 4,522,949, 4,521,539, 4,520,026, 4,517,188, 4,482,562, 4,474,804, 4,474,803, 4,472,411, 4,466,979, 4,463,015, 4,456,617, 4,456,616, 4,456,615, 4,418,076, 4,416,896, 4,252,815, 4,220,594, 4,190,587, 4,177,280, 4,164,586, 4,151,297, 4,145,443, 4,143,054, 4,123,550, 4,083,968, 4,076,834, 4,064,259, 4,064,258, 4,064,257, 4,058,620, 4,001,421, 3,993,639, 3,991,057, 3,982,010, 3,980,652, 3,968,117, 3,959,296, 3,951,950, 3,933,834, 3,925,369, 3,923,818, 3,898,210, 3,897,442, 3,897,441, 3,886,157, 3,883,540, 3,873,715, 3,867,383, 3,873,715, 3,867,383, 3,691,216, 3,624,126;

antimicrobial agents as disclosed in U.S. Pat. Nos. 5,902,594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,746,504, 4,686,221, 4,599,228, 4,552,882, 4,492,700, 4,489,098, 4,489,085, 4,487,776, 4,479,953, 4,477,448, 4,474,807, 4,470,994, 4,370,484, 4,337,199, 4,311,709, 4,308,283, 4,304,910, 4,260,634, 4,233,311, 4,215,131, 4,166,122, 4,141,981, 4,130,664, 4,089,977, 4,089,900, 4,069,341, 4,055,655, 4,049,665, 4,044,139, 4,002,775, 3,991,201, 3,966,968, 3,954,868, 3,936,393, 3,917,476, 3,915,889, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,620 5,665,752, 5,656,661, 5,635,516, 5,631,283, 5,622,948, 5,618,835, 5,607,959, 5,593,980, 5,593,960, 5,580,888, 5,552,424, 5,552,422 5,516,764, 5,510,361, 5,508,026, 5,500,417, 5,498,405, 5,494,927, 5,476,876, 5,472,973, 5,470,885, 5,470,842, 5,464,856, 5,464,849, 5,462,952, 5,459,151, 5,451,686, 5,444,043, 5,436,265, 5,432,181, RE034918, 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,937, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 500654, 4,992,448, 4,992,447, 4,988,733, 4,988,728, 4,981,865, 4,962,119, 4,959,378, 4,954,519, 4,945,099, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598, 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 4,558,067, 4,556,672, 4,556,669, 4,539,326, 4,537,903, 4,536,503, 4,518,608, 4,514,415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,693,648, 5,693,645, 5,691,346, 5,686,469, 5,686,424, 5,679,705, 5,679,640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 5,262,533, 5,260,300, 5,252,732, 5,250,678, 5,247,076, 5,244,896, 5,238,689, 5,219,884, 5,208,241, 5,208,228, 5,202,332, 5,192,773, 5,189,042, 5,169,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

analgesic agents, as disclosed in U.S. Pat. Nos. 5,292,736, 5,688,825, 5,554,789, 5,455,230, 5,292,736, 5,298,522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514 4,147,872, 4,133,819, 4,124,713, 4,117,012, 4,064,272, 4,022,836, 3,966,944;

cholinergic agents, as disclosed in U.S. Pat. Nos. 5,219, 872, 5,219,873, 5,073,560, 5,073,560, 5,346,911, 5,424,301, 5,073,560, 5,219,872, 4,900,748, 4,786,648, 4,798,841, 4,782,071, 4,710,508, 5,482,938, 5,464,842, 5,378,723, 5,346,911, 5,318,978, 5,219,873, 5,219,872, 5,084,281, 5,073,560, 5,002,955, 4,988,710, 4,900,748, 4,798,841, 4,786,648, 4,782,071, 4,745,123, 4,710,508;

adrenergic agents, as disclosed in U.S. Pat. Nos. 5,091, 528, 5,091,528, 4,835,157, 5,708,015, 5,594,027, 5,580,892, 5,576,332, 5,510,376, 5,482,961, 5,334,601, 5,202,347, 5,135,926, 5,116,867, 5,091,528, 5,017,618, 4,835,157, 4,829,086, 4,579,867, 4,568,679, 4,469,690, 4,395,559, 4,381,309, 4,363,808, 4,343,800, 4,329,289, 4,314,943, 4,311,708, 4,304,721, 4,296,117, 4,285,873, 4,281,189, 4,278,608, 4,247,710, 4,145,550, 4,145,425, 4,139,535, 4,082,843, 4,011,321, 4,001,421, 3,982,010, 3,940,407, 3,852,468, 3,832,470;

antihistamine agents, as disclosed in U.S. Pat. Nos. 5,874, 479, 5,863,938, 5,856,364, 5,770,612, 5,702,688, 5,674,912, 5,663,208, 5,658,957, 5,652,274, 5,648,380, 5,646,190, 5,641,814, 5,633,285, 5,614,561, 5,602,183, 4,923,892, 4,782,058, 4,393,210, 4,180,583, 3,965,257, 3,946,022, 3,931,197;

steroidal agents, as disclosed in U.S. Pat. Nos. 5,863,538, 5,855,907, 5,855,866, 5,780,592, 5,776,427, 5,651,987, 5,346,887, 5,256,408, 5,252,319, 5,209,926, 4,996,335, 4,927,807, 4,910,192, 4,710,495, 4,049,805, 4,004,005, 3,670,079, 3,608,076, 5,892,028, 5,888,995, 5,883,087, 5,880,115, 5,869,475, 5,866,558, 5,861,390, 5,861,388, 5,854,235, 5,837,698, 5,834,452, 5,830,886, 5,792,758, 5,792,757, 5,763,361, 5,744,462, 5,741,787, 5,741,786, 5,733,899, 5,731,345, 5,723,638, 5,721,226, 5,712,264, 5,712,263, 5,710,144, 5,707,984, 5,705,494, 5,700,793, 5,698,720, 5,698,545, 5,696,106, 5,677,293, 5,674,861, 5,661,141, 5,656,621, 5,646,136, 5,637,691, 5,616,574, 5,614,514, 5,604,215, 5,604,213, 5,599,807, 5,585,482, 5,565,588, 5,563,259, 5,563,131, 5,561,124, 5,556,845, 5,547,949, 5,536,714, 5,527,806, 5,506,354, 5,506,221, 5,494,907, 5,491,136, 5,478,956, 5,426,179, 5,422,262, 5,391,776, 5,382,661, 5,380,841, 5,380,840, 5,380,839, 5,373,095, 5,371,078, 5,352,809, 5,344,827, 5,344,826, 5,338,837, 5,336,686, 5,292,906, 5,292,878, 5,281,587, 5,272,140, 5,244,886, 5,236,912, 5,232,915, 5,219,879, 5,218,109, 5,215,972, 5,212,166, 5,206,415, 5,194,602, 5,166,201, 5,166,055, 5,126,488, 5,116,829, 5,108,996, 5,099,037, 5,096,892, 5,093,502, 5,086,047, 5,084,450, 5,082,835, 5,081,114, 5,053,404, 5,041,433, 5,041,432, 5,034,548, 5,032,586, 5,026,882, 4,996,335, 4,975,537, 4,970,205, 4,954,446, 4,950,428, 4,946,834, 4,937,237, 4,921,846, 4,920,099, 4,910,226, 4,900,725, 4,892,867, 4,888,336, 4,885,280, 4,882,322, 4,882,319, 4,882,315, 4,874,855, 4,868,167, 4,865,767, 4,861,875, 4,861,765, 4,861,763, 4,847,014, 4,774,236, 4,753,932, 4,711,856, 4,710,495, 4,701,450, 4,701,449, 4,689,410, 4,680,290, 4,670,551, 4,664,850, 4,659,516, 4,647,410, 4,634,695, 4,634,693, 4,588,530, 4,567,000, 4,560,557, 4,558,041, 4,552,871, 4,552,868, 4,541,956, 4,519,946, 4,515,787, 4,512,986, 4,502,989, 4,495,102; the disclosures of which are herein incorporated by reference.

Also of interest are analogs of the above compounds. For all of the above active agents, the active agents may be present as pharmaceutically acceptable salts, as mentioned above.

Delivery Vehicle Component

The delivery compositions of the invention are compositions that are formulated for delivery of an active agent to a topical location, such as a keratinized skin surface or a mucosal surface of a mammalian subject, such as a human subject. By keratinized skin surface is meant a skin location of a subject, i.e., a location of the external covering or integument of an animal body. By mucosal surface is meant a location of a subject that includes a mucosal membrane, such as the inside of the mouth, in the inside of the nose, etc.

Because the dermal delivery formulations of the invention are formulated for delivery to topical location, they are formulated so as to be physiologically compatible with the topical location for which they are formulated. Accordingly, when contacted with the target keratinized skin surface or mucosal surface for which they are formulated, the delivery compositions do not cause substantial, if any, physiological responses (such as inflammation or irritation) that would render the use of the delivery compositions unsuitable for topical application.

The delivery compositions of the invention include an amount of the active agent-calcium phosphate particle complexes included in a delivery vehicle component. The delivery vehicle component refers to that portion of the delivery composition that is not the active agent-calcium phosphate particle complex component.

The delivery vehicle component of the delivery compositions of the invention may vary, as desired, where the particular ingredients of a given delivery vehicle component will depend, at least in part, on the nature of the particular composition. Delivery compositions of interest include liquid formulations, such as lotions (liquids containing insoluble material in the form of a suspension or emulsion, intended for external application, including spray lotions) and aqueous solutions, semi-solid formulations, such as gels (colloids in which the disperse phase has combined with the dispersion medium to produce a semisolid material, such as a jelly), creams (soft solids or thick liquids) and ointments (soft, unctuous preparations), and solid formulations, such as topical patches. As such, delivery vehicle components of interest include, but are not limited to: emulsions of the oil-in-water (O/W) and the water in-oil (W/O) type, milk preparations, lotions, creams, ointments, gels, serum, powders, masks, packs, sprays, aerosols or sticks Lotions Lotions are liquid compositions where the viscosity is 50,000 cP or less, such as 10,000 cP or less, as determined using a Rotational Viscometer, which Measures viscosity by measuring the running torque of the cylindrical rotors immersed in a sample, viscosity determination protocol at a temperature of 25° C., as described in JIS K 7117: Testing Methods For Viscosity With A Rotational Viscometer Of Resins In The Liquid or ASTM D 2196-86:Test Methods for Rheological Properties on Non-Newtonian Materials by Rotational (Brookfield) Viscometer.

Lotion delivery vehicle components of interest may include a number of different ingredients, including but not limited to: water, emollients, natural oils, silicone oils, thickening agents or viscosity modifiers, synthetic or natural esters, fatty acids, alcohols, humectants, emulsifiers, preservative systems, colorants, fragrances, etc. Amounts of these materials may range from 0.001 to 99%, such as from 0.1 to 50%, including from 1 to 20% by weight of the composition, as desired.

Emollients are compounds that replace or add to lipids and natural oils in the skin. The term emollient, as used herein, is intended to include conventional lipid materials (e.g., fats, waxes, and other water insoluble materials), polar lipids (e.g., lipid materials which have been modified to render them more water soluble), silicones and hydrocarbons. Emollients of interest include, but are not limited to: diisopropyl adipate, isopropyl myristate, isopropyl palmitate, ethylhexyl palmitate, isodecyl neopentanoate, $C_{12-15}$ alcohols benzoate, diethylhexyl maleate, PPG-14 butyl ether, PPG-2 myristyl ether propionate, cetyl ricinoleate, cholesterol stearate, cholesterol isostearate, cholesterol acetate, jojoba oil, cocoa butter, shea butter, lanolin, and lanolin esters.

Silicone oils may be divided into the volatile and non-volatile variety. The term "volatile" as used herein refers to those materials which have a measurable vapor pressure at ambient temperature. Volatile silicone oils of interest include but are not limited to: cyclic or linear polydimethylsiloxanes containing from 3 to 9, such as from 4 to 5, silicon atoms. Linear volatile silicone materials may have viscosities of 5 centistokes or less at 25° C., while cyclic materials may have viscosities of 10 centistokes or less. Nonvolatile silicone oils of interest include, but are not limited to: polyalkyl siloxanes, polyalkylaryl siloxanes and polyether siloxane copolymers. The essentially non-volatile polyalkyl siloxanes of interest include, for example, polydimethyl siloxanes with viscosities of 5 to 100,000 centistokes at 25° C.

Suitable esters include, but are not limited to: alkenyl or alkyl esters of fatty acids having 10 to 20 carbon atoms, such as isopropyl palmitate, isopropyl isostearate, isononyl isononanoate, oleyl myristate, oleyl stearate, and oleyl oleate; ether-esters, such as fatty acid esters of ethoxylated fatty alcohols; polyhydric alcohol esters; ethylene glycol mono and di-fatty acid esters; diethylene glycol mono- and di-fatty acid esters, polyethylene glycol (200-6000) mono- and di-fatty acid esters; propylene glycol mono- and di-fatty acid esters, such as polypropylene glycol 2000 monooleate, polypropylene glycol 2000 monostearate, ethoxylated propylene glycol monostearate; glyceryl mono- and di-fatty acid esters; polyglycerol poly-fatty esters, such as ethoxylated glyceryl monostearate, 1, 3-butylene glycol monostearate, 1,3-butylene glycol distearate; polyoxyethylene polyol fatty acid ester; sorbitan fatty acid esters; and polyoxyethylene sorbitan fatty acid esters are satisfactory polyhydric alcohol esters; wax esters such as beeswax, spermaceti, myristyl myristate, stearyl stearate; sterols esters, of which soya sterol and cholesterol fatty acid esters are examples thereof. Both vegetable and animal sources of these compounds may be used. Examples of such oils include, but are not limited to: castor oil, lanolin oil, $C_{10-18}$ triglycerides, caprylic/capric triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like. Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, and PEG glyceryl tallowates.

Fatty acids of interest include, but are not limited to: those having from 10 to 30 carbon atoms, such as pelargonic, lauric, myristic, palmitic, stearic, isostearic, hydroxystearic, oleic, linoleic, ricinoleic, arachidic, behenic and erucic acids.

Humectants of the polyhydric alcohol-type may also find use in the compositions, where examples of polyhydric alcohols include, but are not limited to: glycerol (also known as glycerin), polyalkylene glycols, alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. Also of interest are sugars, e.g., glucose, fructose, honey, hydrogenated honey, inositol, maltose, mannitol, maltitol, sorbitol, sucrose, xylitol, xylose, etc. When present, the amount of humectant may range from 0.001 to 25%, such as from about 0.005 to 20%, including from about 0.1 to 15%, where in some instances the amount of humectant ranges from 0.5 to 30%, such as between 1 and 15% by weight of the composition.

Emulsifiers may also be present in the vehicle compositions. When present, the total concentration of the emulsifier may range from 0.01 to 40%, such as from 1 to 20%, including from 1 to 5% by weight of the total composition. Emulsifiers of interest include, but are not limited to: anionic, nonionic, cationic and amphoteric actives. Nonionic surfactants of interest include those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also of interest nonionic emulsifiers. Anionic emulsifiers of interest include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Where desired, preservatives can include in the compositions, e.g., to protect against the growth of potentially harmful microorganisms. Preservatives of interest include alkyl esters of para-hydroxybenzoic acid, hydantoin derivatives, propionate salts, and a variety of quaternary ammonium compounds. Specific preservatives of interest include, but ar enot limited to: iodopropynyl butyl carbamate, phenoxyethanol, methyl paraben, propyl paraben, imidazolidinyl urea, sodium dehydroacetate, benzyl alcohol, benzylhemiformal, benzylparaben, 5-bromo-5-nitro-1,3-dioxane, 2-bromo-2-nitropropane-1,3-diol,caprylyl glycol, ethylhexylglycerin, phenoxyethanol sorbic acid, methylparaben, propylparaben, ethylpareben, butylparaben, sodium benzoate, potassium sorbate, disodium salt of ethylenediaminetetraacetic acid, chloroxylenol, DMDM Hydantoin, 3-iodo-2-propylbutyl carbamate, chlorhexidine digluconate, phenoxyethanol, diazolidinyl urea, biguanide derivatives, calcium benzoate, calcium propionate, caprylyl glycol, biguanide derivatives, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the likeWhen present, preservatives may be present in the delivery compositions in amounts ranging from about 0.01% to about 10% by weight of the composition.

Thickening agents or viscosity modifiers may be included in the delivery compositions. Thickening agents of interest include, but are not limited to: polysaccharides, such as starches, natural/synthetic gums and cellulosics. Starches of interest include, but are not limited to, chemically modified starches, such as aluminum starch octenylsuccinate. Gums of interest include, but are not limited to: xanthan, sclerotium, pectin, karaya, arabic, agar, guar, carrageenan, alginate and combinations thereof. Suitable cellulosics include, but are not limited to: hydroxypropyl cellulose, hydroxypropyl methylcellulose, ethylcellulose and sodium carboxy methylcellulose. Synthetic polymers are still a further class of effective thickening agent. This category includes cross-linked polyacrylates such as the Carbomers and polyacrylamides such as Sepigel® 305. When present, amounts of the thickener may range from 0.001 to 5%, such as from 0.1 to 2%, including from 0.2 to 0.5% by weight.

In some instances, natural or synthetic organic waxes may be present, e.g., one or more natural or synthetic waxes such as animal, vegetable, or mineral waxes. In some instances, such waxes will have a melting point ranging from 20 to 150° C., such as from 30 to 100° C., including 35 to 75° C. Examples of such waxes include waxes such as polyethylene or synthetic wax; or various vegetable waxes such as bayberry, candelilla, ozokerite, acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, and tribehenin. Also of interest are Acrocomia Aculeata Seed Butter, Almond Butter, Aloe Butter, Apricot Kernel Butter, Argan Butter, Attalea Maripa Seed Butter, Avocado Butter, Babassu Butter, Bacuri Butter, Bagura Soft Butter, Baobab Soft Butter, Bassia Butyracea Seed Butter, Bassia Latifolia Seed Butter, Black Currant Seed Butter, Brazil Nut Butter, Camelina Butter, Camellia Butter, Candelilla Butter, Carnauba Butter, Carpotroche Brasiliensis Seed Butter, Chamomile Butter, Cocoa Butter, Coconut Butter, Coffee Butter, Cotton Soft Butter, Cranberry Butter, Cupuacu Butter, Grape Seed Butter, Hazel Nut Butter, Hemp Seed Butter, Horsetail Butter, Illipe Butter, Irvingia Gabonensis Kernel Butter, Jojoba Butter, Karite Butter, Kokum Butter, Kukui Butter, Lavender Butter, Lemon Butter, Lime Butter, *Macadamia* Butter, Mango Butter, Marula Butter, Monoi Butter, Mowrah Butter, Mucaja Butter, Murumuru Butter, *Olea* Butter, Olive Butter, Orange Butter, Palm Oil, Passion Butter, Phulwara Butter, Pistachio Butter, Pomegranate Butter, Pumpkin Butter, Raspberry Butter, Rice Butter, Sal Butter, Sapucainha Butter, Seasame Butter, Shea Butter, Soy Butter Tamanu Butter, Sunflower Seed Butter, Sweet almond Butter, Tangerine Butter, Tucuma Seed Butter, Ucuuba Butter and Wheat Germ Butter.

Colorants, fragrances and abrasives may also be included in the delivery compositions. Each of these substances may range from 0.05 to 5%, such as from 0.1 and 3% by weight. Colorants of interest include titanium dioxide, where appropriate surface-treated (codified in the Color Index under the reference CI 77,891), manganese violet (CI 77,742), ultramarine blue (CI 77,007), chromium oxide (CI 77,288), hydrated chromium oxide (CI 77,289), ferric blue (CI 77,510), zinc oxide, zirconium dioxide. Specific colorants of interest include: D & C red no. 19 (CI 45,170), D & C red no. 9 (CI 15,585), D & C red no. 21 (CI 45,380), D & C orange no. 4 (CI 15,510), D & C orange no. 5 (CI 45,370), D & C red no. 27 (CI 45,410), D & C red no. 13 (CI 15,630), D & C red no. 7 (CI 15,850:1), D & C red no. 6 (CI 15,850:2), D & C yellow no. 5 (CI 19,140), D & C red no. 36 (CI 12,085), D & C orange no. 10 (CI 45,425), D & C yellow no. 6 (CI 15,985), D & C red no. 30 (CI 73,360), D & C red no. 3 (CI 45,430), carbon black (CI 77,266), cochineal carmine lake (CI 75,470), natural or synthetic melanin, and aluminium lakes.

Fragrances of interest include: *Abies Alba* Leaf Oil, Acetaldehyde, Acetanilid, Acetic Acid, *Achillea Millefolium* Oil, *Actinidia Chinensis* (Kiwi) Fruit Water, Adipic Acid, Agar, Alcohol Denat., Algin, *Aloe Barbadensis* Leaf, Amyl Acetate, Amyl Benzoate, Amyl Cinnamal, Anethole, Anise alcohol, Anthemis Nobilis Flower Water, Benzaldehyde, Benzyl Alcohol, *Betula Alba* Oil, *Boswellia Serrata* Oil, *Butyl Acetate, Butyl Lactate, Calendula Officinalis* Flower Oil, *Camellia Sinensis* Leaf Water, Camphor, Capsaicin, Cedrol, Cinnamal, Citral, Citronellol, *Citrus Aurantifolia* (Lime) Oil, *Citrus Aurantium* Dulcis (Orange) Oil, *Citrus Grandis* (Grapefruit) Oil, *Citrus Tangerina* (Tangerine) Peel Oil, Coumarin, Diacetone Alcohol, Ethyl Cinnamate, Ethyl Ether, *Eucalyptus Caryophyllus* (Clove) Flower Oil, Farnesol, *Gardenia Florida* Oil, *Geranium Maculatum* Oil, Hexyl Cinnamal, Hydrogenated Rosin, *Illicium Verum* (Anise) Oil, Isoamyl Acetate, *Juniperus* Mexicana Oil, *Laurus Nobilis* Oil, *Lavandula angustifolia* (Lavender) Oil, *Melaleuca Alternifolia* (Tea Tree) Leaf Oil, *Melissa Officinalis* Leaf Oil, *Mentha Piperita* (Peppermint) Oil, Menthol, 2-Naphthol, *Origanum Majorana* Leaf Oil, *Panax Ginseng* Root Extract, Pelargonic Acid, *Pelargonim Graveolens* Flower Oil, *Pinus Silvestris* Cone Oil, *Prunus Armeniaca* (Apricot) Kernel Oil, *Rosa Canina* Flower Oil, *Rosmarinus Officinalis* (Rosemary) Leaf Oil, *Santalum Album* (Sandalwood) Oil, *Thymus Vugaris* (Thyme) Oil, Vanillin, *Vitis Vinifera* (Grape) Leaf Oil, *Zingiber Officinale* (Ginger) Root Oil.

Semi-Solid Delivery Compositions

Also of interest are semi-solid delivery compositions, such as gels, creams and ointments. Such compositions may be mixtures of (in addition to the active agent-calcium phosphate particle complex) water, water soluble polymers, preservatives, alcohols, polyvalent alcohols, emulsifying agents, humectants, wax, solvents, thickeners, plasticizers, pH regulators, water-retaining agents and the like. Furthermore, such compositions may also contain other physiologically acceptable excipients or other minor additives, such as fragrances, dyes, emulsifiers, buffers, antibiotics, stabilizers or the like. Examples of these types of compounds are provided above.

Topical Patches

Also of interest are solid formulations, such as topical patch formulations. Topical patch formulations may vary significantly. Topical patch formulations may include an active agent layer, a support and a release liner. The active agent layer may include an amount of the active agent-particle complexes in a matrix, where the matrix may include one or more of: adhesives, such as pressure sensitive rubber and acrylic acids, hydrogels, physiologically acceptable excipients or other minor additives, such as fragrances, dyes, emulsifiers, buffers, antibiotics, stabilizers or the like. The support may be made of a flexible material which is capable of fitting in the movement of human body and includes, for example, plastic films, various non-woven fabrics, woven fabrics, spandex, and the like. Various inert coverings may be employed, which include the various materials which may find use in plasters, described below. Alternatively, non-woven or woven coverings may be employed, particularly elastomeric coverings, which allow for heat and vapor transport. These coverings allow for cooling of the pain site, which provides for greater comfort, while protecting the gel from mechanical removal. The release liner may be made of any convenient material, where representative release films include polyesters, such as PET or PP, and the like.

Aerosol Compositions

Also of interest are aerosol compositions formulations to be administered via inhalation. These aerosol formulations can be placed into pressurized acceptable propellants, such as dichlorodifluoromethane, propane, nitrogen, and the like. They may also be formulated for non-pressured preparations, such as for use in a nebulizer or an atomizer. In some embodiments, the formulations are powdered aerosol formulations which include the active agent bound particles suspended or dispersed in a propellant or a propellant and solvent. The propellant may be a mixture of liquefied chlorofluorocarbons (CFCs) which are selected to provide the desired vapor pressure and stability of the formulation. Propellants 11, 12 and 114 are the most widely used propellants in aerosol formulations for inhalation administration. Other commonly used propellants include Propellants 113, 142b, 152a, 124, and dimethyl ether. The compound 1,1,1,2-tetrafluoroethane is also a commonly used propellant for medicinal aerosol formulations. The propellant may be 40 to 90% by weight of the total inhalation composition.

Methods of Making Delivery Compositions

Aspects of the invention further include methods of making the delivery compositions. While any convenient fabrication protocol may be employed, in some instances fabrication protocols include first preparing the active agent-particle complexes. Following production of the active agent-particle complexes, the resultant complexes are then combined within the delivery composition component using any convenient protocol.

The active agent-particle complexes may be produced using any convenient protocol. One protocol of interest includes first producing a liquid composition of the active agent, such as an aqueous composition of the active agent, and then combining the liquid composition with an amount of uniform, rigid, spherical, nanoporous calcium phosphate particles (with agitation where desired) under conditions sufficient to produce the desired active agent-particle complexes. As such, in certain embodiments a fluid composition of unbound particles, e.g., a slurry of unbound particles in a suitable solvent system (such as an aqueous or non-aqueous solvent system) is combined with a suitable amount of active agent.

Particle Pre-Treatment

As desired, the unbound particles may be pretreated in some manner prior to combination with the active agent. As such, preparation of the active agent bound particles may include a pre-treatment step, such as an initial pH adjustment step. In this step, the unbound particles are modified by contacting them with one or more agents, such as a pH adjustment agent, in order to provide for desired active agent binding to the particles. The particular nature of the pH adjustment, if employed, varies depending on the type of active agent that is to be bound to the particles. One category of active agents of interest are those that include acidic and/or basic charged moieties and a molecular mass greater than a few thousand Daltons, e.g., having a mass of 3000 Daltons or greater, such as 5,000 Daltons or greater, e.g., 10,000 Daltons or greater, 25,000 Daltons or greater, 50,000 Daltons or greater, 75,000 Daltons or greater, 100,000 Daltons or greater, 250,000 Daltons or greater, 500,000 Daltons or greater, 750,000 Daltons or greater, 1,000,000 Daltons or greater. Examples of such active agents include, but are not limited to proteins, nucleic acids and polysaccharides. Such active agents may strongly bind to the calcium and/or phosphate sites of the particles under a broad range of pH conditions. Accordingly, for these types of active agents, pH modification may or may not be performed, as desired. Where pH modification is desired, pH modification may be performed by using any convenient pH adjustment agent, e.g., an acid or alkaline agent. pH adjustment agents of interest include, but are not limited to: lactic acid, glycolic acid, triethanolamine and sodium hydroxide. In some instances, pH adjustment agents are selected that do not block the calcium and/or phosphate binding sites of particles.

Another category of active agents of interest are those that include acidic and/or basic charged moieties and a molecular mass that does not exceed a few thousand Daltons, e.g., having a mass of 2500 Daltons or less, such as 1500 Daltons or less. Examples of such active agents include, but are not limited to organic acid and amine compounds. Such active agents bind to the particles at a specific pH. Pretreatment of the particles by optimizing the pH, and/or addition of specific ionic compounds into the binding solution (described in greater detail below) may be employed, as desired.

Yet another category of active agents of interest are water-soluble small molecules with non-charged or weakly charged moieties. Examples of such compounds include, but are not limited to: saccharides, glycosides and amino acid derivatives. For this category of active agents, an aqueous and/or organic solvent mixture, such as ethanol/water or acetonitrile/water may be employed for a pretreatment and active agent binding, as desired.

Yet another category of active agents of interest are water soluble small molecules with hydrophobic moieties. For such active agents, pretreatment may include contacting the particles with surface modifying agents, e.g., agents that include one or more charged groups and one or more hydrophobic tails, such as but not limited to sodium dodecyl sulfate, sodium lauryl sulfate and sodium lauryl phosphate, and the like.

Yet another category of active agents of interest are water insoluble molecules. Examples of water insoluble molecules of interest include, but are not limited to: amino acid derivatives, polyphenols, and retinoids. For such active agents, the use of organic solvents such as ethanol and dimethyl sulfoxide (DMSO) as a pretreatment agent and/or loading solvent may be employed, as desired.

In some instances, particles are pretreated with an ionic modification agent. Ionic modification agents include, but are not limited to, calcium ion modification agents, such as $CaCl_2$, phosphate ion modification agents, such as sodium phosphate, etc.

Following any particle pretreatment step, e.g., as described above, in some embodiments the particles are subjected to a washing step. For example, in some instances, it may be desirable to remove excess salt or ions from the particles by washing, filtering or decanting the particles prior to active agent binding. Any convenient wash protocol and fluid may be employed for this step.

Complex Formation

Following any pretreatment and/or washing, such as described above (if necessary), the unbound particles are combined with active agent to produce active agent bound particles. The active agent can be either in powder or solution form, as desired. Any suitable protocol for combining the active agent and the particles may be employed, such as simple static mixing in a vessel, etc. The pH of the composition during binding may be selected to provide for maximum binding, e.g., by employing a pH adjustment agent, such as described above. For example, in some instances basic active agents are combined with the particles under basic conditions and acidic active agents are combined with the particles under acidic conditions. Therefore, the pH of the complex formation reaction may range, in some instances from 5 to 14. In certain instances, the pH is 10 or less, where, depending on the length of time employed for complex formation, the pH may be selected so as to avoid substantial particle degradation, e.g., may be selected to be 5.2 or greater.

As indicated above, any convenient solvent system may be employed for producing the active agent-particle complexes. As indicated above, the solvent system employed in binding the active agent to the particles to produce the active agent-particle complexes may vary. Solvent systems finding use in preparing the active agent-particle complexes may be made up of a single solvent or a plurality of two or more different solvents. Solvents that are present in solvent systems of interest may be polar (i.e., they have a dielectric constant of 15 or greater) or non-polar (i.e., they have a dielectric constant of less than 15), and protic (such that they solvate anions (negatively charged solutes) strongly via hydrogen bonding) or aprotic (i.e., they have sufficiently large dipole moments to solvate positively charged species via their dipole).

Protic solvents of interest include, but are not limited to: alcohols, such as methanol, ethanol, propanol, isopropyl alcohol, butanol, pentanol, hexanol, heptanol, octanol, trifluoroethanol, phenol, benzyl alcohol, glycerin, ethylene glycol, diethylene glycol; carboxylic acids/amides, such as formic acid, acetic acid, lactic acid, propionic acid, trifluoroacetic acid, formamide; amines, such as ammonia, diethylamine, butyl amine, propyl amine; and water. Aprotic solvents of interest include, but are not limited to: hydrocarbons, such as pentane, hexanes, heptane, cyclohexane, methyl cyclohexane, decalin; ketones/aldehydes, such as acetone, methyl ethyl ketone (MEK), methyl isobutyl ketone, butanone, pentanone, cyclohexanone, benzaldehyde; aromatic compounds, such as benzene, toluene, trifluorotoluene, xylene, anisole, chlorobenzene, aniline, N,N-dimethylaniline, benzonitrile; ethers, such as dimethoxyethane, dimethyl ether, diethyl ether, diisopropyl ether, methyl t-butyl ether (MTBE), tetrahydrofuran, dioxane, glyme, diglyme, polyethylene glycol (PEG), PEG esters, PEG sorbitans, PEG ethers, PEG esters, polypropylene glycol (PPG), PPG esters, alkoxylated linear alkyl diols, alkoxylated alkyl glucose ether, PPG alkyl ethers; esters/amides, such as methyl acetate, ethyl acetate, propyl acetate, butyl acetate, amyl acetate, ethyl benzoate, benzyl benzoate, dimethyl phthalate, dibutyl phthalate, dimethylacetamide, dimethylformamide (DMF); nitriles, such as acetonitrile; carbonates, such as dimethylcarbonate, diethylcarbonate, propylene carbonate, ethylene carbonate; halogenated compounds, such as carbon tetrachloride, chloroform, dichlormethane, dichloroethane, trichloroethane, freon-11, BMIM-PF$_6$ ionic liquid; sulfur/Phosphorus-containing compounds, such as dimethyl sulfoxide (DMSO), carbon disulfide, sulfolane, examethylphosphramide; and amines, such as pyridine, triethylamine, N-methylpyrrolidinone (NMP)

Solvents of interest include, but are not limited to: alcohol, alcohol denat., benzyl glycol, benzyl laurate, benzyl laurate/myristate/palmitate, 1,4-butanediol, 2,3-butanediol, buteth-3, butoxydiglycol, butoxyethanol, butoxyethyl acetate, n-butyl alcohol, t-butyl alcohol, butyl myristate, butylene glycol, butylene glycol propionate, butyl ethylpropanediyl ethylhexanoate, butyl lactate, butyloctanol, butyloctyl benzoate, butyloctyl salicylate, butyl stearate, butylphthalimide, butyrolactone, $C_{12-15}$ alkyl benzoate, capric acid, caprylic alcohol, cetearyl octanoate, cetyl stearyl octanoate, chlorobutanol, $C_{8-12}$ acid triglyceride, $C_{12-18}$ acid triglyceride, $C_{9-12}$ alkane, $C_{10-13}$ alkane, $C_{13-14}$ alkane, $C_{13-15}$ alkane, $C_{14-17}$ alkane, $C_{14-19}$ alkane, $C_{15-19}$ alkane, $C_{15-23}$ alkane, $C_{18-21}$ alkane, $C_{8-9}$ alkane/cycloalkane, $C_{9-10}$ alkane/cycloalkane, $C_{9-11}$ alkane/cycloalkane, $C_{9-16}$ alkane/cycloalkane, $C_{10-12}$ alkane/cycloalkane, $C_{11-14}$alkane/cycloalkane, $C_{11-15}$ alkane/cycloalkane, $C_{12-13}$ alkane/cycloalkane, $C_{8-10}$alkane/cycloalkane/aromatic Hydrocarbons, $C_{12-15}$ alkane/cycloalkane/aromatic hydrocarbons, $C_{9-10}$ aromatic hydrocarbons, $C_{10-11}$ aromatic hydrocarbons, CD alcohol 19, chlorinated paraffin, $C_{7-8}$ isoparaffin, $C_{8-9}$ isoparaffin, $C_{9-11}$ isoparaffin, $C_{9-13}$ isoparaffin, $C_{9-14}$ isoparaffin, $C_{9-16}$ isoparaffin, $C_{10-11}$ isoparaffin, $C_{10-12}$ isoparaffin, $C_{10-13}$ isoparaffin, $C_{22-12}$ isoparaffin, $C_{11-13}$ isoparaffin, $C_{11-14}$ isoparaffin, $C_{12-14}$ isoparaffin, $C_{12-20}$ isoparaffin, $C_{13-14}$ isoparaffin, $C_{13-16}$ isoparaffin, $C_{20-40}$ isoparaffin, coix lacryma-jobi (Job's Tears) Seed Water, $C_{6-12}$ perfluoroalkylethanol, $C_{10-18}$ triglycerides, cycloethoxymethicone, cycloheptasiloxane, cyclohexanedimethanol, cyclohexasiloxane, cyclomethicone, cyclopentasiloxane, cyclotetrasiloxane, cyclotrisiloxane, decane, 1,10-decanediol, decene, decyl alcohol, deodorized kerosene, diacetin, diacetone alcohol, dibutyl adipate, dibutyloctyl malate, dibutyloctyl sebacate, dibutyl oxalate, dibutyl phthalate, dibutyl sebacate, di-$C_{12-15}$alkyl maleate, diethoxydiglycol, diethoxyethyl succinate, diethylene glycol dibenzoate, diethylhexyl adipate diethylhexyl maleate, diethylhexyl 2,6-naphthalate, diethylhexyl phthalate, diethylhexyl sebacate, diethylhexyl succinate, diethyl oxalate, diethyl phthalate, diethyl sebacate, diethyl succinate, diheptylundecyl adipate, dihexyl adipate, dihexyldecyl sebacate, diisoamyl malate, diisobutyl adipate, diisobutyl oxalate, diisocetyl adipate, diisodecyl adipate, diisononyl adipate, diisooetyl adipate, diisopropyl adipate, diisopropyl oxalate, diisopropyl sebacate, dimethoxydiglycol, dimethyl adipate, dimethyl capramide, dimethyl glutarate, dimethyl isosorbide, dimethyl maleate, dimethyl oxalate, dimethyl phthalate, dimethyl succinate, dimethyl sulfone, dioctyl adipate, dioctyl succinate, dioctyldodecyl sebacate, dioxolane, diphenyl methane, di-PPG-3 myristyl ether adipate, dipropyl adipate, dipropylene glycol, dipropylene glycol dibenzoate, dipropylene glycol dimethyl ether, dipropyl oxalate, ditridecyl adipate, dodecene, echium plantagineum seed oil, eicosane, ethoxydiglycol, ethoxydiglycol acetate, ethoxyethanol, ethoxyethanol acetate, ethylene carbonate, ethyl ether, ethyl hexanediol, ethylhexyl benzoate, ethyl lactate, ethyl macadamiate, ethyl myristate, ethyl oleate, ethyl perfluorobutyl ether, furfural, glycereth-7 benzoate, glycereth-18 benzoate, glycereth-20 benzoate, glycereth-7 diisononanoate, glycereth-4,5-lactate, glycereth-5 lactate, glycereth-7 lactate, glycereth-7 triacetate, glycine soja (soybean) oil, glycofurol, glycol, hexadecene, hexanediol, 1,2-hexanediol, 1,2,6-hexanetriol, hexene, hexyl alcohol, hexyldecyl benzoate, hexyldodecyl salicylate, hexylene glycol, hydrogenated polydecene, hydrogenated polydodecene, hydroxymethyl dioxolanone, isoamyl acetate, isobutoxypropanol, isobutyl acetate, isobutyl benzoate, isobutyl stearate, isocetyl salicylate, isodecyl benzoate, isodecyl isononanoate, isodecyl octanoate, isodecyl oleate, isododecane, isoeicosane, isohexadecane, isononyl isononanoate, isooctane, isopentane, isopentyldiol, isopropyl acetate, isopropyl citrate, isopropyl laurate, isopropyl myristate, isopropyl palmitate, isopropyl phthalimide, isostearyl glycolate, isostearyl stearoyl stearate, laneth-5, lanolin oil, laureth-2 acetate, limonene, 3-methoxybutanol, methoxydiglycol, methoxyethanol, methoxyethanol acetate, methoxyisopropanol, methoxyisopropyl acetate, methoxymethylbutanol, methoxy PEG-7, methoxy PEG-10, methoxy PEG-16, methoxy PEG-25, methoxy PEG-40, methoxy PEG-100, methyl acetate, methylal, methyl benzoate, methylbutenes, methyl gluceth-20 benzoate, methyl hexyl ether, methyl lactate, methyl perfluorobutyl ether, methylpropanediol, methylpyrrolidone, methyl soyate, methyl sunflowerseedate, methyl trimethicone, MIBK, mineral oil, mineral spirits, mixed terpenes, *momordica* grosvenori fruit juice, morpholine, mustelic/palmitic triglyceride, neopentyl glycol, neopentyl glyol dioctanoate, nonocynol-9, octadecane, octadecene, octane, octene, octyl benzoate, octyldodecyl lactate, octyldodecyl octyldodecanoate, octyl isononanoate, octyl isostearate, octyl laurate, octyl palmitate, octyl stearate, oleyl alcohol, olive oil PEG-6 esters, peanut oil PEG-6 esters, PBG-33 castor oil, PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, PEG-350, PEG-400, PEG-450, PEG-500, PEG-2 benzyl ether, PEG-15 butanediol, PEG-3 methyl ether, PEG-4 methyl ether, PEG-6 methyl ether, PEG-7 methyl ether, PEG-50 glyceryl cocoate, PEG-20 hydrogenated castor oil, PEG/PPG-1/2 copolymer, PEG/PPG-4/2 copolymer, PEG/PPG-5/30 copolymer, PEG/PPG-6/2 copolymer, PEG/PPG-7/50 copolymer, PEG/PPG-8/17 copolymer, PEG/PPG-10/70 copolymer, PEG/PPG-17/6 copolymer, PEG/PPG-18/4 copolymer, PEG/PPG-19/21 copolymer, PEG/PPG-23/17 copolymer, PEG/PPG-23/50 copolymer, PEG/PPG-25/30 copolymer, PEG/PPG-26/31 copolymer, PEG/PPG-30/33 copolymer, PEG/PPG-35/9 copolymer, PEG/PPG-38/8 copolymer, PEG/PPG-116/66 copolymer, PEG/PPG-125/30 copolymer, PEG/PPG-160/31 copolymer, PEG/PPG-200/70 copolymer, PEG/PPG-240/60 copolymer, PEG-10 propylene glycol, 1,5-pentanediol, penetaerythrity tetracaprylate/tetracaprate, pentylene glycol, perfluorocaprylyl bromide, perfluorodecalin, perfluorodimethylcyclohexane, perfluorohexane, perfluoromethylcyclopentane, perfluoroperhydrobenzyl tetralin, perfluoroperhydrophenanthrene, perfluorotetralin, petroleum distillates, phenoxyisopropanol, phenylpropanol, polyglyceryl-3 diisostearate, polyglyceryl-2 dioleate, polyoxyethylene glycol dibenzoate, polyperfluoroethoxymethoxy difluoromethyl ether, PPG-3, PPG-7, PPG-10 butanediol, PPG-2-buteth-3, PPG-3-buteth-5, PPG-5-buteth-7, PPG-7-buteth-4, PPG-7-buteth-10, PPG-12-buteth-16, PPG-15-buteth-20, PPG-20-buteth-30, PPG-20 lanolin alcohol ether, PPG-2 myristyl ether propionate, PPG-2 butyl ether, PPG-3 butyl ether, PPG-24-glycereth-24, PPG-25-glycereth-22, PPG-10 glyceryl ether, PPG-55 glyceryl ether, PPG-67 glyceryl ether, PPG-70 glyceryl ether, PPG-2 methyl ether, PPG-3 methyl ether, PPG-2 methyl ether acetate, PPG-2 propyl ether, propanediol, propyl acetate, propylene carbonate, propylene glycol, propylene glycol butyl ether, propylene glycol caprylate, propylene glycol dibenzoate, propylene glycol methyl ether, propylene glycol myristate, propylene glycol propyl ether, *ricinus communis* (castor) seed oil, SD Alcohol 1, SD Alcohol 3-A, SD Alcohol 3-B, SD Alcohol 3-C, SD Alcohol 23-A, SD Alcohol 23-F, SD Alcohol 23-H, SD Alcohol 27-B, SD Alcohol 30, SD Alcohol 31-A, SD Alcohol 36, SD Alcohol 37, SD Alcohol 38-B, SD Alcohol 38-C, SD Alcohol 38-D, SD Alcohol 38-F, SD Alcohol 39, SD Alcohol 39-A, SD Alcohol 39-B, SD Alcohol 39-C, SD Alcohol 39-D, SD Alcohol 40, SD Alcohol 40-A, SD Alcohol 40-B, SD Alcohol 40-C, SD Alcohol 46, sea water, *sesamum indicum* (sesame) oil, shark liver oil, sorbeth-6, sorbeth-20, sorbeth-30, sorbeth-40, sorbitan trioleate, stearyl benzoate, stearyl heptaroate, tetradecene, tetradecylpropionates, tetrahydrofurfuryl acetate, tetrahydrofurfuryl alcohol, thiolanediol, triacetin, tributyl citrate, tributylcresylbutane, trichloroethane, triethyl phosphate, trimethylhexanol, 2,2,4-timethylpentane, trimethyl pentanol hydroxyethyl ether.

Where desired, the solvent system can be modified with one or more modification agents, such as buffers, pH adjusters (acid or base), hydrophilic molecules, hydrophobic molecules or the molecules which have both hydrophobic groups and hydrophilic groups (e.g., surfactants). Buffers of interest include, but are not limited to: HCl/sodium citrate, citric acid/sodium citrate, acetic acid/sodium acetate, $K_2HPO_4/KH_2PO_4$, $Na_2HPO_4/NaH_2PO_4$, Borax/Sodium hydroxide, as well as biological buffers, e.g., TAPS (3{[tris (hydroxymethyl)methyl]amino}propanesulfonic acid), Bicine (N,N-bis(2-hydroxyethyl)glycine), Tris(tris(hydroxymethyl)methylamine), Tricine (N-tris(hydroxymethyl) methylglycine), HEPES (4-2-hydroxyethyl-1-piperazineethanesulfonic acid), TES (2-[tris(hydroxymethyl) methyl]amino}ethanesulfonic acid), MOPS (3-(N-morpholino)propanesulfonic acid), PIPES (piperazine-N,N-bis(2-ethanesulfonic acid), Cacodylate (dimethylarsinic acid), SSC (saline sodium citrate) and MES (2-(N-morpholino)ethanesulfonic acid); etc.

The components and properties of a particular solvent system, such as pH, composition, temperature, etc., can be selected in view of one or more properties of the active agent to be complexed with the particles, where such properties may include active agent solubility, structure, pKa, logP, etc.

Following production of the active agent-particle complexes, the resultant complexes are then combined with the delivery composition component using any convenient protocol. The particular protocol employed may vary depending on the nature of the delivery composition component, where in certain instances the delivery composition component and active agent loaded particles may be combined with mixing to produce the desired delivery composition. While the temperature during combination may vary, in some instances the temperature is 80° C., such as 40° C. or less, such as 30° C. or less, e.g., room temperature or colder. The amount of active agent-particle complexes that is combined with the delivery vehicle may vary. In some embodiments, the amount of active agent-particle complexes that is combined with the delivery vehicle sufficient to produce a final delivery composition in which the amount of active agent-particle complexes ranges from 0.001 mg/g to 1000 mg/g, such as 0.1 mg/g to 200 mg/g and including 1 mg/g to 50 mg/g active agent-particle complexes per gram of delivery composition component. In certain embodiments, the presence of chelating agents is avoided. The pH of formulation is 5.0 or greater, such as 5.5 or greater.

Utility

The delivery compositions of the invention find use in methods of delivering active agents to a topical location of a subject, where the topical location may be a skin surface location or a mucosal location. In delivering active agents to a topical location of a subject, delivery compositions of the invention may deliver the active agent-particle complexes at least into an epidermal location that is beneath the skin surface of a subject. As such, embodiments of the invention include methods of delivering active agent loaded particles into the stratum corneum of a subject, where the methods may result in delivery of the complexes into the deep stratum corneum and/or dermis of a subject. By "into the stratum corneum" is mean that the complexes are delivered to a region that is at least 1 cell layer below the skin surface. By "deep stratum corneum" is meant a region that is 2 or more cell layers below the skin surface, such as 5 or more cell layers below the skin surface, including 10 or more cell layers below the skin surface. In some instances, the complexes are delivered to region of the stratum corneum that is 2 µm or more such as 5 µm or more and including 15 µm or more below the surface of the skin.

Embodiments of the invention include methods of delivering active agent loaded particles into the stratum corneum of a subject, where the methods may result in delivery of the complexes into the dermis of a subject. By "into the dermis" is meant that the complexes are delivered to a region that is at least 20 cell layers below the skin surface.

Upon reaching their target dermal location, in some instances the active agent bound particles begin to release their active agent "payload". Release of the active agent from the particles may occur according to a number of different mechanisms. For example, the environment of the skin may reverse any binding interaction of the agent to the particle. In addition to this mechanism or alternatively to it, the environment of the skin may break down the calcium phosphate particles (e.g., via dissolution caused by pH gradient of the skin), such that the uniform, rigid, spherical, nanoporous particles dissolve under acidic conditions, e.g., conditions of pH 5 or lower, such as 4.5 or lower, including 4.3 or lower, such as the physiological acidic conditions of the stratum corneum. The time required for dissolution of particles in the stratum corneum may vary, and in certain embodiments ranges from 1 minute to 72 hours, such as 10 minutes to 24 hours and including 30 minutes to 12 hours, over which time period active agent is released from the active agent bound particles. Aspects of the invention include release of all active agent.

Methods of the invention therefore result in delivery of an active agent at least into the stratum corneum of a subject. In some embodiments, the active agent remains in the stratum corneum to exert its desired activity. In yet other embodiments, the active agent may exert its desired activity at one or more other target locations of the body. Additional target locations interest include additional epidermal regions, such as but not limited to the stratum lucidum, stratum granulosum, stratum spinusom, stratum basale and dermis. In certain embodiments, the active agent is delivered to a region of the dermis. In certain embodiments, the active agent is delivered to a region below the dermis, e.g., into sub-cutaneous tissues.

In some instances the active agent may be systemically delivered to the subject. When the active agent is systemically delivered to the subject, therapeutic plasma levels of active agent are achieved. Therapeutic plasma levels of active agent may vary depending on the particular active agent and condition being treated. In certain embodiments, therapeutic active levels that are achieved range from 0.1 pg to 100 µg, such as 1 pg to 20 µg, such as 1 ng to 1 µg and including 10 ng to 100 ng.

In practicing methods of the invention, a delivery composition is applied to a topical region of a subject and maintained at the topical region in a manner sufficient to result in the desired delivery of the active agent to the subject, as described above. The topical region is, in certain embodiments, a keratinized skin region. The keratinized skin region, including hair follicles, sweat glands and sebaceous glands, may be present at a variety of intact or damaged skin locations, where locations of interest include, but are not limited to: limbs, arms, hands, legs, feet; torso, e.g., chest, back, stomach; head, e.g., neck, face; etc. In certain embodiments, the region will be a head region, such as a facial region, e.g., forehead, occipital region, around the mouth, etc. The topical region to which the composition is applied may vary with respect to area, ranging in certain embodiments from 1 mm$^2$ to 300 cm$^2$ or more, such as from 1 cm$^2$ to 50 cm$^2$, and including from 3 cm$^2$ to 10 cm$^2$.

In practicing the subject methods, a subject may be administered a single dose or two or more doses over a given period of time. For example, over a given treatment period of one month, 1 or more doses, such as 2 or more doses, 3 or more doses, 4 or more doses, 5 or more doses, etc., may be applied to a topical location of the subject, where the doses may be applied weekly or daily or even multiple times per day.

Delivery of active agent complexes in accordance with the present invention may impart one or more advantages as compared to a control which the active agent is not delivered as a complex with calcium phosphate particles. For example, in some instances the active agent is stabilized in the calcium phosphate complexes, such that its activity is preserved. In some instances, the complexing the active agent with calcium phosphate particle in complexes according to embodiments of the invention provides for delivery of the active agent to locations in which it would not normally be delivered, e.g., delivery into the stratum corneum where delivery would be limited to the skin surface if that agent were not present in a calcium phosphate particle complex. In some instances, methods of the invention result in enhanced penetration of the active agent as compared to a suitable control. A suitable control may be a delivery composition that includes the same active agent and delivery vehicle components, but lacks the uniform, rigid, spherical, nanoporous calcium phosphate particles. In some instances, penetration is enhanced as compared to such a control by a factor of 2-fold or more, such as 5-fold or more, including 10-fold or more. In yet other embodiments, the complexes serve as a controlled release depot of active agent from the stratum corneum, thereby providing desired extended release and delivery profiles for an active agent.

While the active agent-calcium phosphate complexes have been described herein primarily in terms of their use for dermal delivery applications, in some instances they are employed for other applications. For example, the active agent-calcium phosphate complexes of the invention find use in some instances in non-dermal delivery of active agents to a subject. Examples of non-dermal delivery formulations include, but are not limited to: capsules, tablets, pills, pellets, lozenges, powders, granules, syrups, elixirs, solutions, suspensions, emulsions, suppositories, or sustained-release formulations thereof, or any other form suitable for administration to a mammal. In some instances, the pharmaceutical compositions are formulated for administration in accordance with routine procedures as a pharmaceutical composition adapted for oral or intravenous administration to humans. Examples of suitable pharmaceutical vehicles and methods for formulation thereof are described in Remington: The Science and Practice of Pharmacy, Alfonso R. Gennaro ed., Mack Publishing Co. Easton, Pa., 19th ed., 1995, Chapters 86, 87, 88, 91, and 92, incorporated herein by reference.

In certain embodiments, methods of delivering calcium into at least into the stratum corneum are provided. In these methods, intact calcium phosphate particles of the invention are delivered into at least the stratum corneum, e.g., as described above. By "intact" is meant that the particles are full integrity, undamaged particles. As such, they will not be the same as particles that have been contacted with a chelating agent, such as EDTA, where the chelating agent compromises the structure of the particles, e.g., by action of the chelating action with the calcium ions. In these embodiments, the calcium phosphate particles may be free of any bound active agent, e.g., they are calcium phosphate particles that are not associated with an active agent. In these embodiments, the delivery vehicle component may be free of any chelating agent, e.g., EDTA. These methods find use in delivery calcium into at least the stratum according for any convenient purpose, and may be performed on subjects that are desirous of delivering calcium into at least the stratum corneum. Any of the delivery vehicles described above may be employed, where those vehicles that are free of a chelating agent are of interest.

The subject methods and compositions may be used in a variety of different kinds of animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects or patients are humans.

The following examples are offered by way of illustration and not by way of limitation.

EXPERIMENTAL

I. Production and Characterization of Uniform, Rigid, Spherical, Nanoporous Calcium Phosphate Particles
A. Production A calcium phosphate nano-crystal slurry was prepared by dropwise addition of an aqueous phosphate complex solution into an aqueous calcium complex solution or suspension under controlled conditions of temperature, pH, pressure, gas, stirring velocity, reagent concentration, addition rate and aging time. The slurry was spray dried to form a spherical porous powder by using a pressure nozzle type spray dryer with an air-liquid fluid nozzle. The dried powder was sintered at temperature ranging 300 to 900° C. for a period of time ranging 1 to 24 hours with gas or electric furnace or kiln.

B. Characterization

Figure 1B:
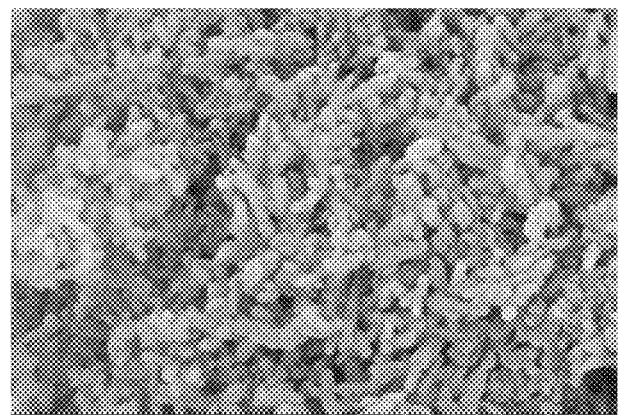
Figure 2A:
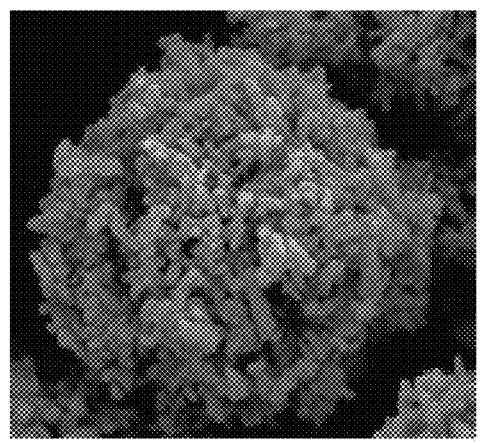
Figure 2B:
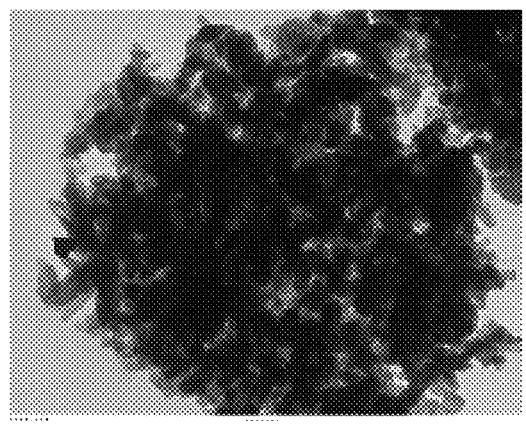
Figure 3:
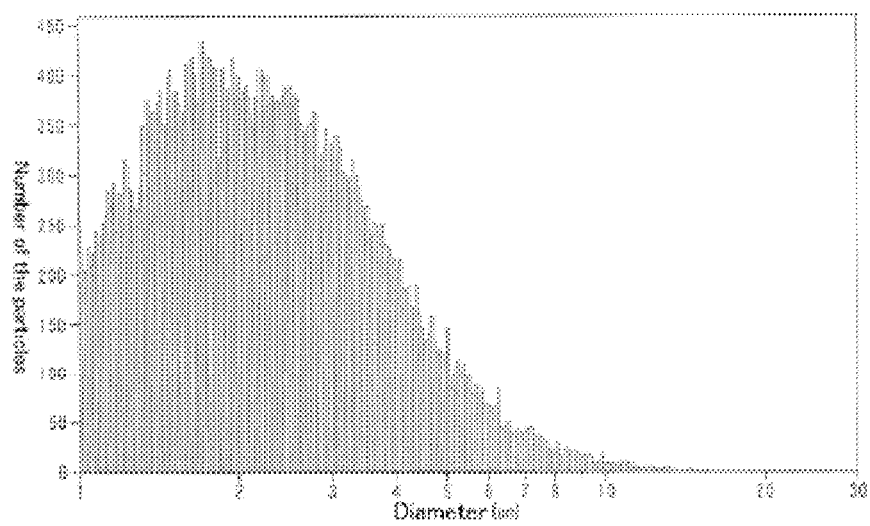
FIG. 3 provides a graphical representation of the particle size distribution of uniform, rigid, spherical, nanoporous calcium phosphate particles that find use in delivery compositions of the invention.

FIGS. 1A and 1B show the porous structure of the resultant 2 micron uniform, rigid, spherical, nanoporous calcium phosphate particles (produced as described above) using SEM (A) 10,000×, (B) 50,000×. FIGS. 2A and 2B show the outside and inside structure of the 2 micron uniform, rigid, spherical, nanoporous calcium phosphate particles (produced in as described above) using both SEM (A) and TEM (B) (15000×). The large (25-50 m²/g) internal and external surface areas are substantial, allowing for high capacity binding with active agents. FIG. 3 shows the particle size distribution of the particles, as determined by Coulter Multi-sizer 3 particle counter and confirmed by scanning electron microscopy. The average particle size was 2 μm.

C. Safety of Calcium Phosphate Particles

| Cytotoxicity | US-FDA 21 CFR Part 58 | Non Toxic |
| Mutagenicity | Ames Test | Non Mutagenic |
| Skin Sensitization | RIPT (Human) | Non Irritating |

II. Preparation of Active Agent-Calcium Phosphate Particle Complexes
A. General Binding Guidelines Including Pre-treatment of certain Active Agents Calcium phosphate particles bind a broad range of biomolecules and in some instances stabilizes them. The binding with calcium phosphate particles is based on ionic interaction. The functional groups of calcium phosphate particles consist of positively charged calcium ions ($Ca^{++}$), and negatively charged phosphate ion ($PO_4^{-3}$). This means the amount of the anionized carboxyl group of the biomaterials will be reduced under acidic conditions. Thus the binding between anionized carboxyl group of the biomolecules and calcium ion of calcium phosphate particles will be weakened. The situation is reversed for the interaction between the cationized amino group of the biomolecule and phosphate functional group of calcium phosphate particles in basic conditions.

The pH and ionic strength directly influence the binding between calcium phosphate particles and biomaterials. Calcium phosphate particles have the ability to bind biomaterials with a broad range of molecular weights (e.g., 200 to 10,000,000) and isoelectric points (e.g., 2.0 to 12).

In addition to pH and ionic strength, the molecular weight, shape, and the orientation of biomaterials also influence the binding to calcium phosphate particles. For example, BSA with relatively low molecular weight bind at 90 mg/g and DNA at a relatively large molecular weight binds to calcium phosphate particles at the rate of 1 mg/g. The binding capacity of large biomolecules such as DNA will be determined by the outer surface area of calcium phosphate particles. To summarize, the main parameters influencing the binding between calcium phosphate particles and biomolecules are pH, ionic strength, the stereochemical effect, and molecular weight.

B. Specific Active Agent-Calcium Phosphate Particle Complexes
1. Influence of pH on Binding
a. Salicylic Acid
Materials:
Calcium Phosphate Particles
Salicylic acid, Fisher Scientific, Part No. A277-500
Methods:
i. 23.2 mg of Salicylic acid was dissolved in 1 ml of ethanol.
ii. 4 g of calcium phosphate particles were suspended in 39.8 ml of water and the pH was adjusted close to the targeted pH with HCl.
iii. 0.2 ml of Salicylic acid solution (23.2 mg/ml) was mixed in the suspension of calcium phosphate particles.
iv. The pH was adjusted to each of the target pH values (11.36, 8.34, 7.47, 7.07, 5.99) with HCl.

v. At each pH, a 4.8 ml sample was taken from the suspension. All the samples were centrifuged separately at 2000×g for 10 min.
vi. The absorbance of supernatant was measured at 297 nm (the detection wavelength for Salicylic acid) by UV spectrophotometer.
vii. The control was carried out by the same procedures without calcium phosphate particles.

Results:
The results are shown in the table below and demonstrate that Salicylic acid binds to calcium phosphate particles in a pH dependent manner driven by the pKa of Salicylic acid.

| pH | Salicylic acid Bound (ug/g) |
|---|---|
| 11.36 | 1141.14 |
| 8.34 | 660.4 |
| 7.47 | 97.5 |
| 7.07 | 23.8 |
| 5.99 | 0 | b. Polyphenol Complex (PPC) to Calcium Phosphate Particles

Materials:
Calcium Phosphate Particles
Polyphenol complex (PPC)

Methods:
i. 33.98 mg of PPC was dissolved in 6.8 ml of water.
ii. 2 g of calcium phosphate particles were suspended in 19.9 ml of water and the pH was adjusted to pH 9.62 with HCl.
iii. 0.1 ml of PPC solution (5 mg/ml) was mixed in the suspension of calcium phosphate particles; a 2 ml sample was taken.
iv. The pH was adjusted to each of the target pH values (8.58, 8.07, 7.49, 7.21, 6.75, 6.08) with HCl.
v. At each pH, a 2 ml sample was taken from the suspension. All the samples were centrifuged separately at 2000×g for 10 min.
vi. The absorbance of each supernatant was measured at 280 nm (the detection wavelength for PPC) by UV spectrophotometer.
vii. The control was carried out by the same procedures without calcium phosphate particles.

Results:
Binding capacity of calcium phosphate particles is summarized in the table below. The results demonstrate that PPC binding can be carried out at any pH, and is therefore pH independent.

| pH | PPC bound (µg/g) |
|---|---|
| 9.62 | 242.5 |
| 8.58 | 242.5 |
| 8.07 | 235.0 |
| 7.49 | 215.0 |
| 7.21 | 220.0 |
| 6.75 | 212.5 |
| 6.08 | 197.5 |

2. Binding Examples of Protein Actives with different Molecular Weights (MW) and Isoelectric Points (pI)

a. Bovine Serum Albumin (BSA) (MW: 66 KD, pI: 4.7)

Materials:
Calcium Phosphate Particles
BSA, lypholized powder, Fisher Scientific, Catalog No. BP-671-10

Methods:
i. 0.5 g of calcium phosphate particles was suspended in 1 ml of water, pH was adjusted with HCl to approximately 7. The suspension was mixed for 10 min.
ii. BSA was dissolved in water and gently mixed to prepare a 20 mg/ml solution. 4 ml of the BSA solution was added into each suspension of calcium phosphate particles, and mixed for 30 min. The final pH of the suspension was determined.
iii. The suspension was centrifuged at 2000×g for 5 min. The supernatant was transferred to new tubes and centrifuged again at 2000×g for 5 min.
iv. A size-exclusion HPLC method was developed to quantify BSA in the supernatants of the binding suspensions. The separation was performed using a Phenomenex Bio-Sep™-SEC-S3000 column (7.8×300 mm, 5 µm) in the Shimadzu 10AS system. The mobile phase was 100% 50 mM phosphate buffer ($Na^+$, pH 6.8), and eluted at a rate of 1.4 ml/min. The eluent was monitored at 280 nm. BSA was observed as a major peak with retention time at about 6.8 min. The quantification of BSA was achieved by external standard calibration.
v. The control was carried out by the same procedure without calcium phosphate particles.

Results:
BSA bound to calcium phosphate particles at 95.1 mg/g.

b. Lactoferrin (MW: 90 KD, pI: 8.5)

Materials:
Calcium Phosphate Particles
Lactoferrin from human milk, Sigma Aldrich, Catalog No. 0520-100MG Methods:
i. Lactoferrin solution was prepared in water at 4.98 mg/ml.
ii. 0.3 g of Calcium phosphate particles was suspended in 1.2 ml of water and mixed for 5 min.
iii. 1.8 ml of Lactoferrin solution at 4.98 mg/ml was added to achieve the final concentrations at 3.0 mg/ml, and the final volume was 3 ml.
iv. The suspension was mixed for 30 min, and centrifuged at 5000×g for 10 min in a bench top centrifuge.
v. The absorbance of supernatant was measured at 280 nm (the detection wavelength for Lactoferrin) by UV spectrophotometer.
vi. The control was carried out by the same procedures without calcium phosphate particles.
vii. Lactoferrin bound was calculated by subtracting the amount of the Lactoferrin detected in the supernatant from the total initial amount in the binding suspension.

Results:
29.63 mg/g Lactoferrin was determined bound to calcium phosphate particles at a binding concentration of 2.99 mg/ml.

c. Lysozyme (MW: 14 KD, pI: 10.7)

Materials:
Calcium Phosphate Particles
Lysozyme, MP biomedicals LLC. Product No. ICN10083405
Phosphoric acid, Fisher Scientific, Product No. A260500

Methods:
i. 364.7 mg of Lysozyme as dissolved in 18.01 ml of water (20.25 mg/ml).
ii. 0.8 g of calcium phosphate particles were mixed with 4 ml of water, and the pH of the suspension was adjusted to neutral with diluted phosphoric acid.
iii. 4 ml of Lysozyme solution (20.25 mg/ml) was added to the suspension of calcium phosphate particles to achieve a final concentration of 10.124 mg/ml, and a final volume of 8 ml. The final pH was measured.

iv. The suspension was mixed for 30 min, and centrifuged at 2000×g for 10 min in a bench top centrifuge.

v. The absorbance of supernatant was measured at 280 nm (the detection wavelength for Lysozyme) by UV spectrophotometer.

vi. The control was carried out by the same procedures without calcium phosphate particles.

Results:

Lysozyme was determined bound to calcium phosphate particles at 6.8 mg/g at pH 6.83.

3. Influence of Solvent on Binding

Adapalene

Materials:

Calcium Phosphate Particles

Adapalene, Sekhsaria Chemicals Limited, India

DMSO, Fisher Scientific, Product No. D159-4

Ethanol, Fisher Scientific, Product No. AC61511-0010

Methods:

i. Adapalene was prepared as saturated solutions in ethanol and DMSO (0.087 mg/ml in ethanol, 20.65 mg/ml in DMSO)

ii. 0.5 g of calcium phosphate particles were mixed with 5 ml of the Adapalene saturated solution in ethanol or DMSO.

iii. The suspensions were mixed for 30 min, and centrifuged at 2000×g for 10 min in a bench top centrifuge.

iv. The absorbance of supernatants were measured at 319 nm (the detection wavelength for Adapalene) by UV spectrophotometer.

v. The controls were carried out by the same procedures without calcium phosphate particles.

Results:

Binding capacity of Adapalene to calcium phosphate particles in ethanol is 0.78 mg/g. Binding capacity of Adapalene to calcium phosphate particles in DMSO is 12.55 mg/g.

C. Example of Pretreatment of Bioactives

Argireline to calcium phosphate particles was pretreated with sodium lauryl sulfate Materials:

Calcium Phosphate Particles

Argireline, (Acetyl Hexapeptide-8), Lipotec S.A.

Sodium lauryl sulfate (SLS), Colonial Chemical, Inc.

Methods:

i. Argireline was dissolved in water as a 10 mg/ml solution.

ii. Calcium phosphate particles were mixed with 10 ml of 0.1% SLS for 5 min. The suspension was centrifuged at 2000×g for 10 min in the bench top centrifuge, and the supernatant was removed. The pellet was re-suspended in 20 ml water, centrifuged at 2000×g for 10 min, and the washing supernatant was discarded. The washing step was repeated twice. The water contained in the pellet was determined. The final pellet was used in the binding study.

iii. Calcium phosphate particles (SLS treated or no SLS treatment) were mixed with water. HCl (or NaOH) was added to adjust the pH of Calcium phosphate particles suspension to targeted pH including neutral and pH ~10.

iv. Argireline stock at 10 mg/ml was added to each binding suspensions to be a final concentration of 0.5 mg/ml. After the suspension was mixed for 30 min, the final pH was measured.

v. The binding suspensions were centrifuged at 2000×g for 10 min in the bench top centrifuge. The supernatants were analyzed with Refractive Index detector connected to the Shimadzu HPLC 20A system to quantify the free Argireline in the solution. A size-exclusion HPLC method was developed to quantify Argireline in the supernatants of the binding mixtures. The separation was achieved using a Phenomenex BioSep™-SEC-S3000 column (7.8×300 mm, 5 μm) in the Shimadzu 20A system. The mobile phase was 100% water, and eluted at a rate of 1 ml/min. The eluent was monitored at 205 nm or by a refractive index detector (Shimadzu, Model No. RID-10A). Argireline was observed as a major peak in the chromatogram with retention time of about 14 min. The quantification of Argireline was achieved by external standard calibration.

vi. The Argireline bound was then calculated by subtracting the amount of Argireline detected in the supernatant from the total initial amount in the binding suspension.

Results:

| Calcium phosphate particles | pH | Argireline bound (mg/g) |
| --- | --- | --- |
| SLS treated | 7.85 | 1.19 |
| SLS treated | 10.10 | 2.15 |
| No pretreatment | 7.39 | 0.09 |
| No pretreatment | 10.46 | 0.05 |

Figure 4:
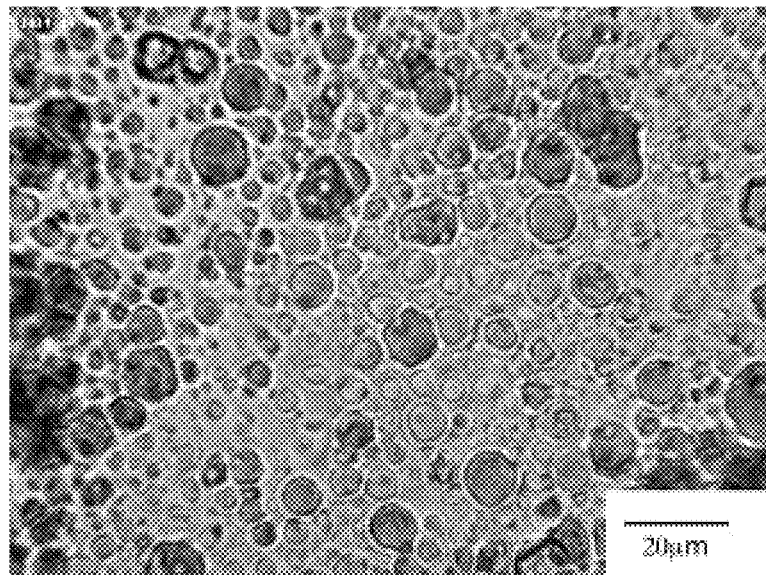
FIG. 4A shows a visual image of active agent attached to calcium phosphate particles.
FIG. 4B shows a visual image of active agent attached to calcium phosphate particles.
Figure 4:
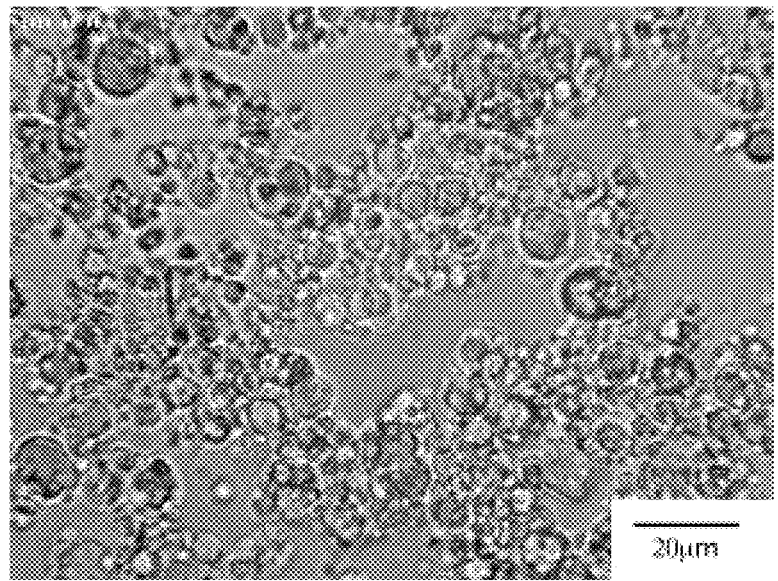

D. Visualization of Active Agent bound to Calcium Phosphate Particles 0.1 g of calcium phosphate particles was added to 1 ml 0.9% Rhodamine B in water, and the resultant suspension was spun and the supernatant was removed. The resultant Rhodamine B-calcium phosphate particles were dried at 58° C. for 24 hours. The resultant powder was resuspended in Caprylic/Capric Triglyceride and imaged via microscopy. The resultant image is shown in FIG. 4A. FIG. 4B shows calcium phosphate particles without any Rhodamine B.

E. Additional Active Agent-Calcium Phosphate Complexes

Using the protocols illustrated above, active agent-calcium phosphate complexes were produced as summarized in the following tables. In the following tables, the specific solvent systems are examples of solvent systems that may be used.

| Classes | Active Name | Solvent |
| --- | --- | --- |
| 534-1. Azo Compounds | Sulfasalazine | Ethanol |
| 534-1. Diazo Compounds | Azaserine | Water |
| 536-2. Carbohydrate derivatives | Dextran sulfate sodium salt MW 20000 | Water |
| 536-2. Carbohydrate derivatives | Hyaluronic Acid, Low MW | Water |
| 536-2. Carbohydrate derivatives | Hyaluronic Acid, High MW | Water |
| 536-3. Glycosides | Doxorubicin hydrochloride (Adriamycin) | Water |
| 536-4. Oxygen-containing hetero ring | Uridine 5'-diphosphoglucose disodium salt | 10 mM Bis-Tris Buffer |

| Classes | Active Name | Solvent |
| --- | --- | --- |
| 536-5. Flavon sugar compounds | Riboflavin 5'-monophosphate | 10 mM Bis-Tris Buffer |
| 536-5. Flavon sugar compounds | Rutin hydrate | Ethanol |
| 540-6. Steroidal hetero compounds | Sodium Cholesteryl Sulfate | Ethanol |
| 540-7. Azaporphyrins | Cyanocobalamin | Acetonitrile |
| 540-8. Four-membered lactam with a vicinyl halogen | Cefaclor | Water |
| 540-9. Nitrogen hetero rings of more than six members (can include multiple heteroatoms) | GYKI 52466 hydrochloride | Water |
| 544-10. Hetero ring is six-membered having two or more ring heteroatoms of which at least one is nitrogen | Thiamine Pyrophosphate | Water |
| 544-11. Six-membered hetero ring consists of oxygen, sulfur, nitrogen and carbon | Acesulfame K | Acetonitrile |
| 544-12. Six-membered hetero ring consists of sulfur, nitrogen and carbon | Methylene Blue | Acetonitrile |
| 544-13. Six-membered hetero ring consists of oxygen, nitrogen and carbon | Furaltadone | Dichloromethane |
| 544-14. Six-membered hetero ring consists of nitrogen and carbon | Ciclopirox Olamine | Water |
| 544-15. Hetero ring is six-membered consisting of one nitrogen and five carbons | Nicotine | Water |
| 548-16. Hetero ring is five-membered having two or more ring hetero atoms of which at least one is nitrogen | Imiquimod | Ethanol |
| 548-18. Hetero ring is three-membered having two or more ring hetero atoms of which at least one is nitrogen | (1R)-(−)-(10-Camphorsulfonyl)oxaziridine | DMSO |
| 549-19. Sulfur containing hetero ring (e.g., thiiranes, etc.) See above. | Amoxicillin | Acetonitrile |
| 549-20. Oxygen containing hetero ring (e.g., oxirane, etc.) See above | (−)Scopolamine methyl nitrate | Water |
| 549-20. Oxygen containing hetero ring (e.g., oxirane, etc.) See above | Calcein | Water |
| 552-21. Azides | AZT (Azidothymidine or Zidovudine) | DMSO |
| 552-22. Triphenylmethanes | o-Cresolphthalein Complexone | 10 mM Bis-Tris Buffer |
| 552-23. Tetracyclo naphthacene configured ring system having at least one double bond between ring members | Minocycline Hydrochloride (HCl), | 10 mM Bis-Tris Buffer |
| 552-23. Tetracyclo naphthacene configured ring system having at least one double bond between ring members | Chlortetracycline HCl | Water |
| 552-24. Quinolines, Hydrocarbon | Difloxacin HCl | Water |
| 552-25. Steroids | CHAPS (3-[(3-Cholamidopropyl)dimethylammonio]-1-propanesulfonate) | Acetonitrile |
| 554-26. Fatty compounds having an acid moiety which contains the carboxyl of a carboxylic acid, salt, ester, or amide group bonded directly to one end of an acyclic chain of at least seven uninterrupted carbons. | Lecithin (L-α Phosphatidylcholine) | Octanol |

-continued

| Classes | Active Name | Solvent |
|---|---|---|
| 556-27. Heavy metal, aluminum, or silicon organic compounds. | Carboplatin | Acetonitrile |
| 558-28. Thioimidate esters | Sinigrin Hydrate | Water |
| 558-29. Imidate esters | Ethyl Benzimidate Hydrochloride | DMSO |
| 558-30. Thiocyanate esters | Allyl isothiocyanate | Hexane |
| 558-31. Sulfate esters | β-Estradiol 3-sulfate sodium salt | DMSO |
| 558-32. Sulfonate esters | Alizarin Red S | Water |
| 558-33. Phosphorus esters (phosphonate, phosphonic acid) | Alendronic Acid | Acetonitrile-1M NaOH |
| 558-35. Nitrate esters or chalcogen analogues | Norcandil | DMSO |
| 560-36. Carboxylic acid esters | Methyl Salicylate | Ethanol |
| 560-37. Sulfonic acids, salts, halides | Chondroitin sulfate A sodium salt | Water |
| 560-38. Sulfohydroxamate esters or chalcogen analogues | Sulfadimethoxine | Isopropyl Alcohol |
| 560-39. Perhydroxamate esters or chalcogen analogues | 6-Aminonicotinamide | Acetonitrile-1M HCl |
| 562-40. Organic acids | Salicylic acid | Acetonitrile |
| 562-40. Organic acids | L-Arginine | Water |
| 562-40. Organic acids | L-Histidine | Acetonitrile-1M HCl |
| 562-40. Organic acids | DPHP (Dipalmitoyl Hydroxyproline) | Ethanol |
| 562-40. Organic acids | Adapalene | DMSO |
| 562-40. Organic acids | Ca PCA (Calcidone) | Water |
| 562-41. Acid halides, acid anhydrides | Poly[(isobutylene-alt-maleic acid, ammonium salt)-co-(isobutylene-alt-maleic anhydride)], average Mw ~60,000 | Acetonitrile |
| 562-42. Selenium or Tellurium compounds | Seleno-DL-cystine | IPA-1M HCl; Acetic Acid-1M HCl |
| 564-43. Ureas | Allantoin | DMSO |
| 564-44. Sulfonamides, sulfamides | Sumatriptan Succinate | Acetonitrile |
| 564-45. Nitro-containing compounds | 2-Nitrophenyl β-D-glucopyranoside | Isopropyl Alcohol |
| 564-46. Carboxamides | Z-L-Asparagine | Acetonitrile-Water |
| 564-47. Oxyamines | Methoxyamine hydrochloride | Acetonitrile |
| 568-48. Boron, Phosphorus, Sulfur, or Oxygen compounds | Resveratrol | Ethanol |
| 568-48. Boron, Phosphorus, Sulfur, or Oxygen compounds | ATP (Adenosine Triphophate) | Water |
| 568-48. Boron, Phosphorus, Sulfur, or Oxygen compounds | ADP (Adenosine Diphosphate) | Water |
| 568-48. Boron, Phosphorus, Sulfur, or Oxygen compounds | AMP (Adenosine Monophosphate) | Water |
| 568-48. Boron, Phosphorus, Sulfur, or Oxygen compounds | Zoledronic acid | Acetonitrile-1M NaOH |
| 570-49. Halogen containing organic compounds | Diclofenac | Acetonitrile |
| 424-50. Lymphokines | Gamma Globulins from bovine blood | Water |
| 424-51. Enzyme or coenzyme | Thrombin Topical (Recombinant) | Water |
| 424-51. Enzyme or coenzyme | Superoxide dismutase | Water |
| 424-52. Extract, body fluid, or cellular material of undetermined constitution derived from animal is active ingredient | Catalase | Water |
| 424-52. Extract, body fluid, or cellular material of undetermined constitution derived from animal is active ingredient | Goat IgG | Water |
| 424-53. Inorganic active ingredient containing composition, e.g. metal | Bacitracin zinc salt | Acetonitrile-1M HCl |
| 424-53. Inorganic active ingredient containing composition, e.g. metal | Copper phthalocyanine | Water |
| 424-54. Extract or material containing or obtained from a multicellular fungus as active ingredient | Streptomycin sulfate salt | Acetonitrile |
| 435-55. Enzyme (e.g., ligases, etc.), proenzyme; | Sulfatase | Water |
| 435-55. Enzyme (e.g., ligases, etc.), proenzyme; | Phosphatase | Water |

-continued

| Classes | Active Name | Solvent |
|---|---|---|
| 435-55. Enzyme (e.g., ligases, etc.), proenzyme; | Lysozyme | Water |
| 435-56. Virus or bacteriophage, except for viral vector or bacteriophage vector; composition thereof; | Bacteriophage CE6 λ phage for delivery of T7 RNA polymerase | Water; 20 mM Na Phosphate Buffer |
| 435-57. Micro-organism | Ampicillin sodium | Water |
| 435-57. Micro-organism | Gentamicin sulfate from Micromonospora purpurea | Water |
| 530-58. Peptides of 3 to 100 amino acid residues | Lys-Lys-Lys | Acetonitrile |
| 530-58. Peptides of 3 to 100 amino acid residues | Argireline | Water |
| 530-59. Peptides containing unnatural amino acid residues or derivatives | N-Acetylmuramyl-L-alanyl-D-isoglutamine hydrate (Muramyl Dipeptide) | Ethanol |
| 530-60. Peptides containing non-linear or heterogeneous backbone elements | Cyclosporin A | Hexane |
| 530-61. Peptide-like structures containing terminal functionalization(s) | Boc-Gly-Lys-Arg-7-amido-4-methylcoumarin hydrochloride | Acetonitrile |
| 530-62. Proteins, i.e., more than 100 amino acid residues | Lactoferrin (human precursor reduced) | Water |
| 530-62. Proteins, i.e., more than 100 amino acid residues | BSA | Water |
| 530-62. Proteins, i.e., more than 100 amino acid residues | Ovalbumin | Water |
| 530-62. Proteins, i.e., more than 100 amino acid residues | Phycoerythrin | Water |
| 426. Food or edible material: processes, compositions, and products | Fermented soybean extract | Water; Glycerin |
| 426. Food or edible material: processes, compositions, and products | *Aloe Vera* (Botanivera 1-200C) | Water |
| 426-63. Product for promoting the effect of an alimentary canal microorganism Product with added vitamin or derivative thereof for fortification | Ascorbic Acid (Vitamin C) | Water |
| 426-63. Product for promoting the effect of an alimentary canal microorganism Product with added vitamin or derivative thereof for fortification | Sodium Ascorbyl Phosphate (Stay-C) | Water |
| 426-63. Product for promoting the effect of an alimentary canal microorganism Product with added vitamin or derivative thereof for fortification | Potassium Ascorbyl Tocopheryl Phosphate (Sepivital) | Water |
| 426-63. Product for promoting the effect of an alimentary canal microorganism Product with added vitamin or derivative thereof for fortification | Disodium Ascorbyl Sulfate (VC-SS) | Water; Acetonitrile |
| 426-63. Product for promoting the effect of an alimentary canal microorganism Product with added vitamin or derivative thereof for fortification | Ubiquinol | Hexane |
| 426-64. Predominantly hydrocarbon compounds containing cyclic carbon rings; three-, four-, five-, six- or more membered rings. | Ursolic Acid | DMSO |

| No | Actives | Loading Solvent | Optimum pH | Structural classes |
|---|---|---|---|---|
| 1 | Ascorbic acid | Water | >8.12 | Sugar acids |
| 2 | Salicylic Acid | Ethanol/water | 4.03-7.90 | Aromatic acids |
| 3 | Hyaluronic acid Sodium salt | Water | 7 | Polysaccharide |
| 4 | Hyaluronic acid Sodium salt | Water | 7 | Polysaccharide |
| 5 | Argireline | Water | 6.7-7.8 | Peptides |
| | | Water | 7.8 | |
| | | Water | 6.4 | |
| 6 | Fermented Soybean Extract | Glycerin | 7 | Proteins |
| 7 | Sepivital (dl-a-tocopheryl 2 L ascorbyl phosphate) | Water | 7 | Vitamin derivatives |
| 8 | Sepilift DPHP (dipalmitoyl hydroxyproline) | Ethanol | | Amino acid derivatives |
| 9 | Resveratrol | Ethanol/water | 10 | Polyphenol |
| 10 | Bovine serum albumin | Water | 7 | Proteins |
| 11 | Chlortetracycline | Water | pH 7-8.5 | Tetracycline antibiotic, |
| 12 | Ciclopirox Olamine | Water | 7 | Alkaloids |
| | | Water | pH 8.5 | |
| | | Water | pH 8.5 | |
| | | Water | pH 9.1 | |
| | | Water | pH 8.9 | |
| 13 | Adapalene | Ethanol | 11 | Retinoids |
| | | Ethanol | 7 | |
| | | DMSO | 7 | |
| 14 | Imiquimod | Ethanol | 11 | Alkaloids |
| | | Ethanol | 70.8 | |
| 15 | Adriacin | Water | | |
| 16 | Alpha lipoic acid | Water | | |
| 17 | Green tea polyphenol | Water | | Polyphenol |
| 18 | Matrixyl Acetate (PalmitoylPentapeptide, PAL-Lys-Thr-Thr-Lys-Ser) | Water | | Peptide |
| 19 | Oleic acid | No solvent | | Fatty acid |
| 20 | Oleyl oleate | No solvent | | Fatty acid |
| 21 | Dextran | Water | | polysaccharide |
| 22 | Ascorbic acid glucoside | Water | | Vitamin C derivative |

III. Release of Active Agent

A. pH Dependent Release

1. Lysozyme

In the stratum corneum, the pH ranges from approximately 4.3 to 5.0 with pH decreasing with stratum corneum depth. To study calcium phosphate particle release active agent at conditions analogous to skin, two lysozyme calcium phosphate complexes were exposed to buffers of ph 4.8 (0.5 M sodium acetate) and 7.0 (10 mM Bis Tris) for 8 hours. The buffers flowed through the samples at a rate of 1 mL/hr and were collected hourly and analyzed for lysozyme release by monitoring the peak at 280 nm by UV spectrometer. An equivalent mass of lysozyme Calcium phosphate particles complex was vortexed in pH 4.8 buffer to estimate the total available lysozyme in the sample. At pH 4.8, lysozyme was observed to quickly release from the calcium phosphate particles with most of the lysozyme releasing within the first hour. In contrast, at pH 7, no lysozyme is observed released from calcium phosphate particles over 8 hours.

B. Release via Hydroxysome Degradation

1. Calcium Phosphate Particles Degrade at pH 4.8

50 mg of calcium phosphate particles were incubated in 2 mL at two pHs: 4.8 (0.5 mM sodium acetate) and 7.1 (0.1 mM Bis Tris) and the solutions place on a rotator for 96 hours at room temperature. The samples were centrifuged and the pellet dried and weighed. The percent weight loss of calcium phosphate particles at pH 4.8 and 7.1 was 12% and 3%, respectively. The buffering capacity of this closed system limited the complete dissolution of the calcium phosphate particles. Dissolution was then studied in a flow-through system with the same buffer whereby the solution was slowly (5 mL/hr) flowed through the sample (50 mg) with gentle agitation of the sample followed by collection and drying of the calcium phosphate particle pellet. After 72 hours, the percent weight loss of calcium phosphate particle pellet at pH 4.8 and 7.1 was 31% and 3%, respectively. These results demonstration that calcium phosphate particles dissolve at low pH and this dissolution is a function of the pH and buffering capacity of the solution.

C. Active Agent is Reversibly Bound to Calcium Phosphate Particles and Release does not Alter Activity of Active Agent 1. BSA Calcium Phosphate Complex BSA-calcium phosphate complexes were prepared as above. The resultant complexes were washed with water and then treated with 0.2 M sodium phosphate to release any bound BSA.

Materials:

Calcium Phosphate Particles

BSA, lypholized powder, Fisher Scientific, Catalog No. BP-671-10

Methods:

i. 0.1170 g of BSA was dissolved in 11.7 ml of water as a solution of 10 mg/ml.

ii. 0.5 g of calcium phosphate particles were mixed with 5 ml of BSA solution at 10 mg/ml. The suspension was mixed for 30 min and the final pH was determined to be neutral.

iii. The suspension was centrifuged at 2000×g for 10 min. The supernatant was transferred to new tubes and centrifuged again at 2000×g for 10 min.

iv. The final supernatant was analyzed with Shimadzu 10A HPLC system to quantitate BSA and calculate the binding.

v. The pellet from 5 ml of binding suspension was mixed with 0.8 ml of water, and centrifuged at 2000×g for 10 min. The rinsed pellet was mixed again with 0.8 ml of water and centrifuged at 2000×g for 10 min.

vi. The final rinsed pellet was mixed with 2 ml of 500 mM sodium phosphate buffer (pH 6.8) and 2.235 ml of water to release BSA in a suspension with 200 mM sodium phosphate. The release suspension was centrifuged at 2000×g for 10 min. The supernatant was analyzed with Shimadzu 10A HPLC system to quantitate BSA.

v. The BSA quantitation was achieved using a Phenomenex BioSep™-SEC-S3000 column (7.8×300 mm, 5 μm) in the Shimadzu 10AS system. The mobile phase was 100% 50 mM phosphate buffer (Na$^+$, pH 6.8), and eluted at a rate of 1.4 ml/min. The eluent was monitored at 280 nm. BSA was observed as a major peak with retention time at about 6.8 min. The quantification of BSA was achieved by external standard calibration.

vi. The control was carried out by the same procedures without calcium phosphate particles.

Results:

The released BSA was analyzed with HPLC and determined to be identical to an unbound control (retention time at 6.85 min), demonstrating that binding and release to calcium phosphate particles did not impact BSA integrity.

2. Sodium Tocopheryl Phosphate Calcium Phosphate Complex

Materials:
Calcium Phosphate Particles
Sodium Tocopheryl Phosphate (TPNa), Showa Denko KK
Ethanol, Fisher Scientific, Product No. AC615090020

Methods:
i. 20 mg of TPNa was dissolved in 40 ml of water by gently mixing (0.5 mg/ml).
ii. 3 g of calcium phosphate particles was mixed with 30 ml of TPNa solution at 0.5 mg/ml, and mixed for 30 min.
iii. The binding suspension was centrifuged at 2000×g for 10 min. The supernatant was transferred to new tube, and centrifuge again at 2000×g for 10 min to clarify. The final supernatant was analyzed with an UV spectrophotometer at 286 nm to quantitate free TPNa and calculate the binding. Approximately 100% of TPNa in the binding suspension was attached to calcium phosphate particles.
iv. The pellet of TPNa calcium phosphate complex was re-suspended in 60% ethanol to release the bound TPNa.
v. The release suspension in 60% ethanol was centrifuged at 2000×g for 10 min. The supernatant was analyzed with an UV spectrophotometer at 286 nm to quantitate free TPNa released.

Results:
The released TPNa was analyzed with UV spectroscopy and determined to be identical to an unbound control, demonstrating that binding and release to calcium phosphate particles did not impact TPNa integrity.

IV. Examples of Formulations
1. Calcium Phosphate Particle—Riboflavin Monophosphate Ointment Formulation

|   | Trade Name | INCI Name | w/w % |
|---|---|---|---|
| 1 | Bee wax | Bee wax | 5.00 |
| 2 | SonneNatural ™ | Glyceride oils | 74.66 |
| 3 | Protachem IPP | Isopropyl Palmitate | 15.00 |
| 4 | Capmul MCM | Glyceryl Caprylate/Caprate | 3.33 |
| 5 | Purified Water | Water | 1.00 |
| 6 | calcium phosphate particles | Hydroxyapatite | 1.00 |
| 7 | Riboflavin Monophosphate | Riboflavin monophosphate | 0.0077 |

Procedure:
Step 1. In a beaker add Bee wax and Protachem IPP. Start to heat to 70° C.-75° C. until uniform. Cool to 50° C. Add SonneNatural™ and Capmul MCM. Mix until uniform.
Step 2. In a separate beaker add 1% water and Riboflavin monophosphate. Mix at R.T until dissolved. Add calcium phosphate particle (adjust pH with lactic acid to pH 7). Spin for 10 minutes at 500 RPM.
Step 3. Transfer Step 1 to Step 2 under room temperature. Mix until uniform B. Stability of Active Agent in Formulation
1. Vitamin C
a. Methods:
11.9 mg of ascorbic acid was dissolved in 30 ml of water. 2 g of 2 μm calcium phosphate particles were suspended in 19.5 ml of water and the pH was adjusted to pH 7.14 with HCl. 0.5 ml of ascorbic acid solution (0.40 mg/ml) was mixed in the suspension of calcium phosphate particles, which reduced the pH to 7.05. The suspension (pH 7.05) of calcium phosphate particles including 10 μg/ml of ascorbic acid was incubated at 50° C. for 0.5 to 5 hours. The heat-denaturation of ascorbic acid was terminated by cooling the suspension in an ice bath for 15 minutes. In order to release bound ascorbic acid from calcium phosphate particles to measure the stabilization effect, the pH of each suspension was adjusted to pH 5 with HCl and centrifuged at 3,000 rpm for 10 minutes. The supernatant obtained was measured at 265 nm. As a control, a 10 μg/ml of ascorbic acid solution was also incubated and measured by the same procedures without calcium phosphate particles. The activity of ascorbic acid was calculated by the following formula:

$$\text{The activity of ascorbic acid}(\%) = (A_{265nm} \text{ of the supernatant after incubation}/A_{265nm} \text{ of the ascorbic acid before incubation}) \times 100$$

The same procedures were repeated with 10 μm calcium phosphate particles.

b. Results
The results are summarized in the table below. The activity of Ascorbic acid was reduced to 36% by incubation at 50° C. for 0.5 hrs; this activity was increased to 85% when ascorbic acid was attached to 2 μm calcium phosphate particles during the same period. The ascorbic acid without calcium phosphate particles was totally denatured with no activity after the incubation at 50° C. for 3 hrs. However, the ascorbic acid bound to 2 μm calcium phosphate particles had 48% activity at 50° C. for the same 3 hr period.

| Time (hrs) | Control (%) | 2 um (%) |
|---|---|---|
| 0 | 100 | 100 |
| 0.5 | 36 | 85 |
| 2 | 18 | 59 |
| 3 | 0 | 48 |
| 5 | 0 | 35 |

C. In order to achieve stability of the active in the calcium phosphate complex in final formulation, it may be necessary to add additional free active to the solvent system depending on the solubility of the solvent system used.

Figure 5A:
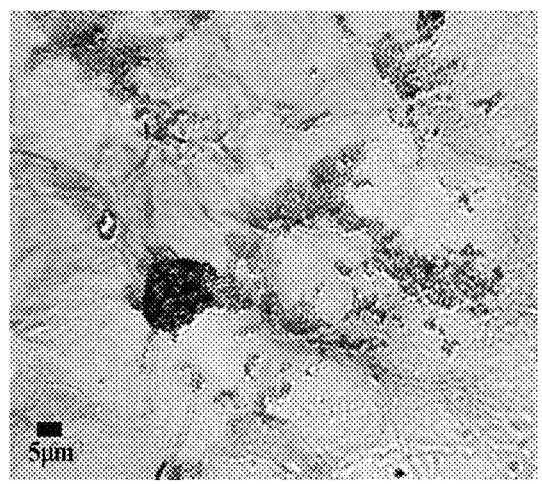
FIGS. 5A and 5B show the tape strip images following application of a 10% calcium phospahte particle slurry to the forearm.
Figure 5B:
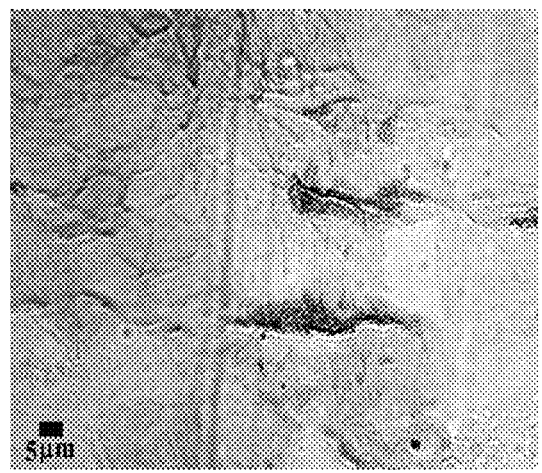
Figure 6:
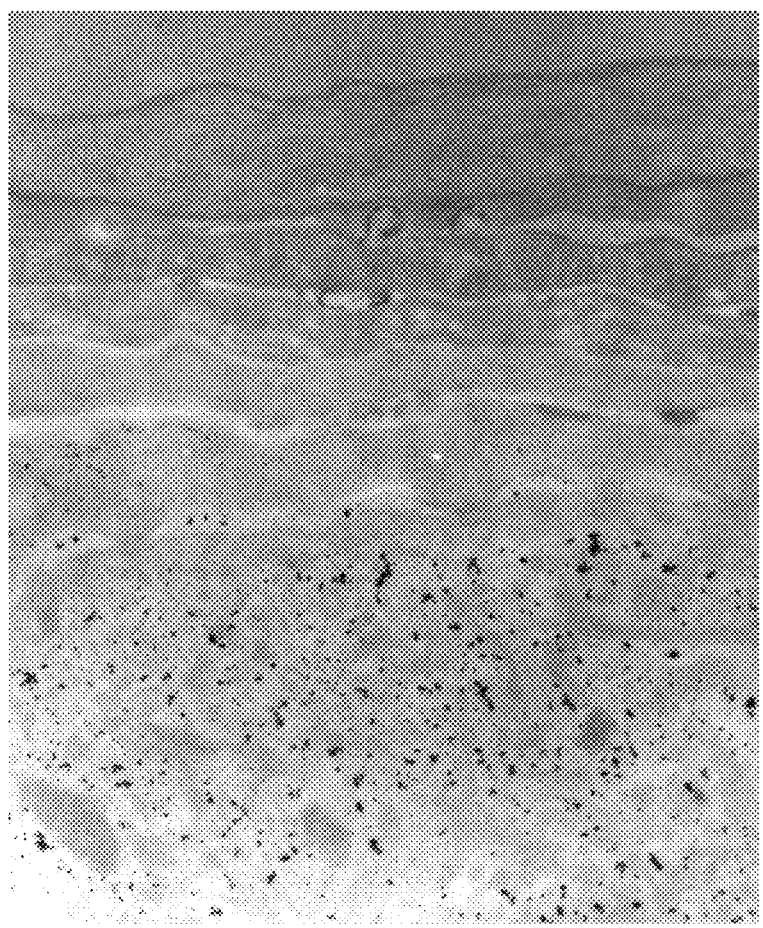
FIG. 6 is an image of mouse skin prior to application of calcium phosphate particles. No $Ca^{++}$ is evident in the upper statum corneum.
Figure 7A:
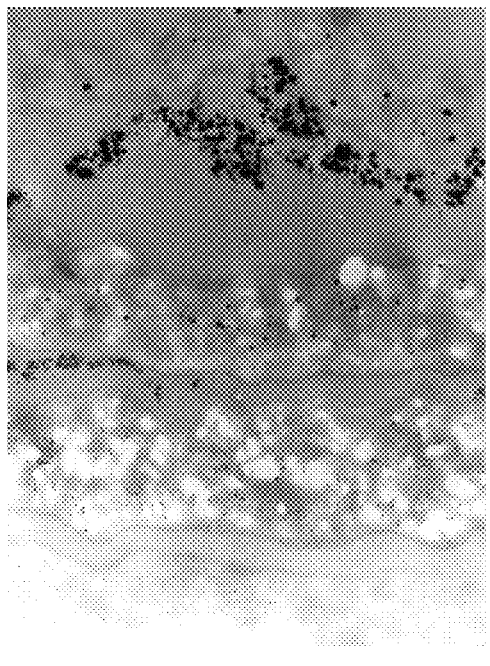
FIG. 7A shows calcium particles in the upper stratum corneum as well as smaller particles in the lower stratum corneum.
Figure 7B:
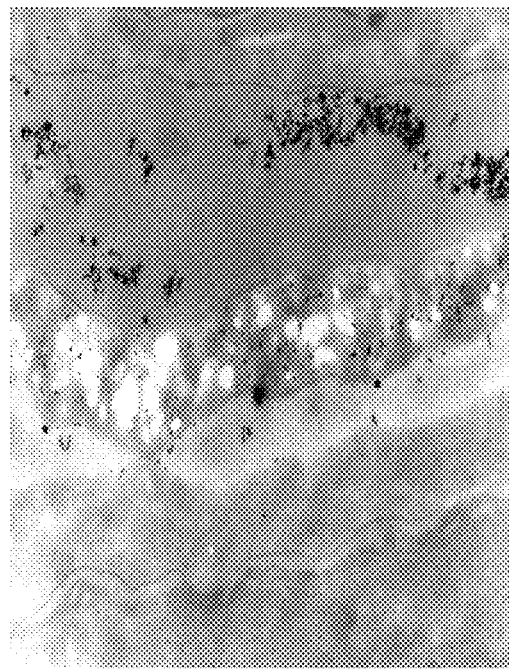
FIG. 7B shows the loss of integrity of the spherical calcium particles

V Delivery Studies
1. Delivery into Stratum Corneum in Human Skin
A suspension of calcium phosphate particles in water at a concentration was applied to a forearm of a living human by rubbing for 10 seconds (FIG. 5). Tape stripping of the first, second and third layers of the stratum corneum was then performed. The calcium phosphate particles penetrated to the third layer of the stratum corneum.
2. Delivery into Lower Layers of Stratum Corneum in Mouse Skin
Calcium phosphate particles penetrate the stratum cornuem and penetrate further into the lower layers as the particle disintegrates into smaller substituent parts. Calcium phosphate particles were no longer intact after 7 hours and were no longer spherical, indicating loss of the integrity of the particles.
a. Materials:
2 μm calcium phosphate particles were used.
b. Preparation:
The calcium phosphate particles were suspended in 70% Ethylene glycol and 30% Ethanol to make a 10% suspension. The resultant suspension was topically applied on the skin surface of hairless mice (1×1 cm area). During the application, mice were given anesthetic. The first application (0.2 ml) was administrated and left on, the second application was administrated 4 hours later at the same place and for the same amount. Seven hours from the first application the skin was removed, and treated by the $Ca^{++}$. Localization method followed by EM techniques.

c. Results:

Prior to treatment with calcium phosphate particles, examination of the epidermis reveals only in the areas of Stratum granulosum, with no detectable $Ca^{++}$ in stratum cornum (FIG. 6). After topical application of calcium phosphate particles as described above, calcium phosphate particles can be seen in the stratum corneum (FIG. 7A), with the smallest particles moving into deeper layers (FIG. 7B).

3. Active agent detection in the stratum corneum a. Purpose of Study

The purpose of this study was to detect active agent (chlorotetracycline (CTC)) in the stratum corneum after the topical application of active agent (CTC) attached to 2 μm uniform, rigid, spherical, nanoporous calcium phosphate particles, as described in Example I, above. Chlortetracycline (CTC from Sigma, part #C-4881) was selected because it allows the visualization of CTC by fluorescence and is thus detectable by confocal microscopy within the stratum corneum.

b. Preparation

A CTC solution was made by dissolving 80 mg of CTC in 10 ml of water. The un-dissolved CTC was removed by centrifugation at 3,000 rpm for 10 min. 200 mg of particles were mixed with 2 ml of the CTC solution and vortexed for 1 min. The free CTC was removed by 3 cycles of washing with water followed by centrifugation for 10 min at 3,000 rpm. The resultant CTC bound particles were suspended in water at 1:10 dilution rate.

c. Topical Application

The suspension produced in 3.b above (approximately 0.2 ml) was topically applied onto the skin of hairless mice (1×1 cm area). During the application, mice were given anesthetic. After 7 hours their skins were examined using confocal microscopy (at 510 nm wavelength emission excited at 380 nm wavelength).

d. Results

Figure 8:
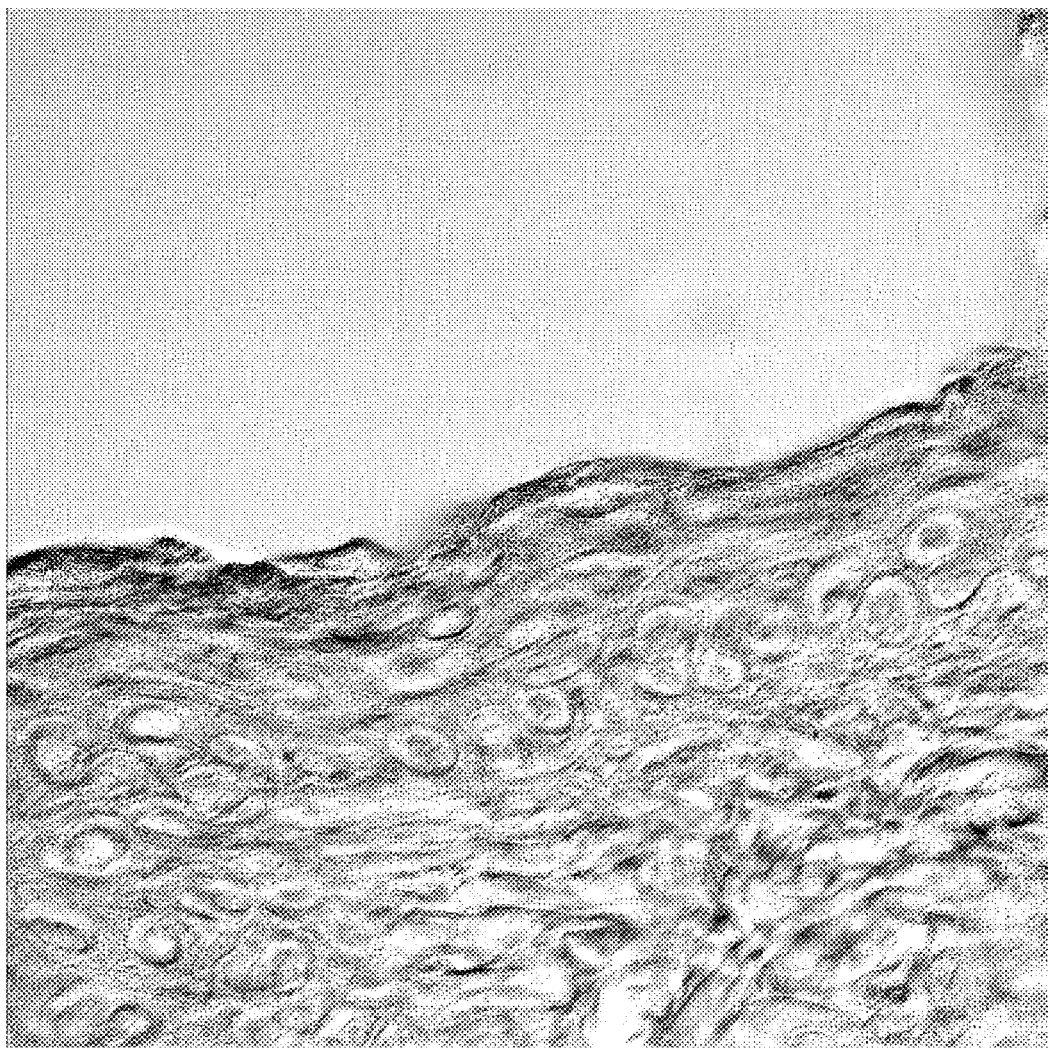
FIG. 8 is a picture showing penetration of CTC fluorescent throughout the stratum corneum following topical application.

The resultant confocal microscopy image is shown in FIG. 8 (magnification is 300× in FIG. 8). The representative image shown in FIG. 8 shows that CTC fluorescence (purple) penetrates the skin and is mainly localized in the stratum corneum.

Figure 9:
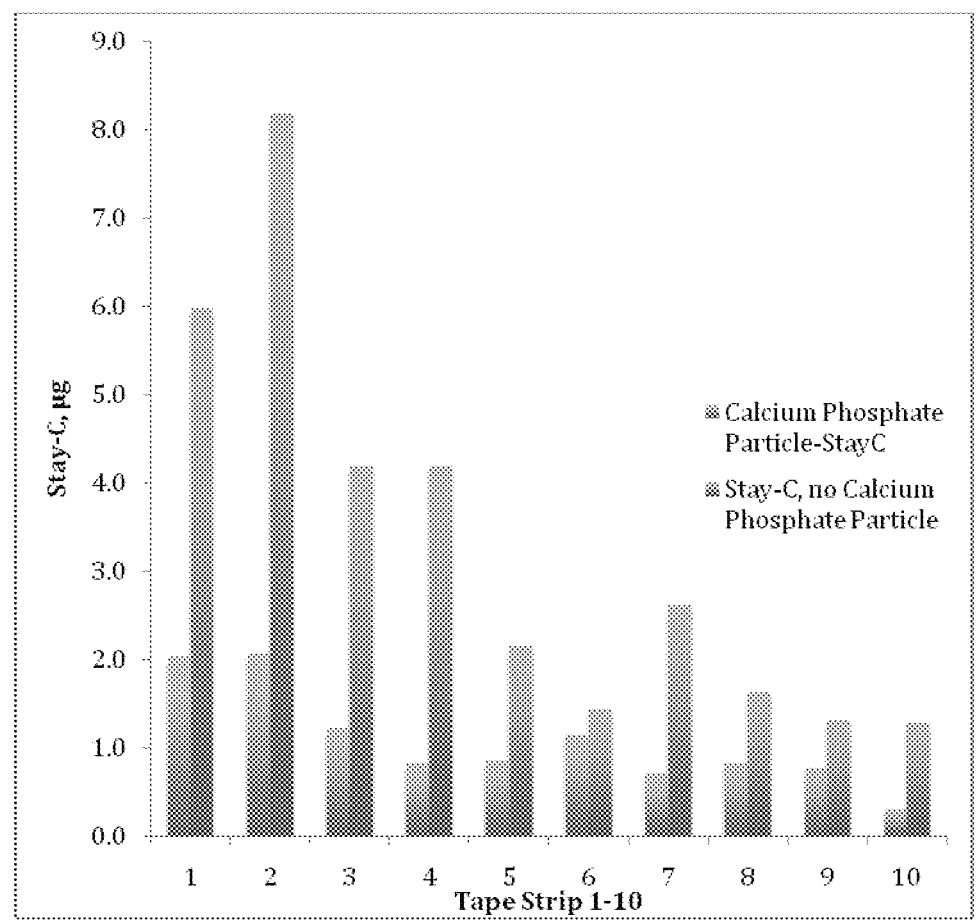
FIG. 9 shows the results of STAY-C50 with and without calcium phosphate particle tape stripping.

4. Tape-stripping analysis of topical application of STAY-C50-calicum phosphate and lysozyme-calcium phosphate complexes demonstrate delivery into the stratum corneum The purpose of this study was to detect the distribution of actives in the stratum corneum following topical application of the active-calcium phosphate particles Method: The distribution of STAY C50 within the stratum corneum was assessed by serial tape stripping of the skin to which a STAY C50-calcium phosphate particle formulation was applied. An application site on the forearm of a human subject was marked and 200 μl of the formulation spread by spatula. The site was allowed to dry for 10 minutes and then followed by ten pre-weighed tape stripping using strips of (3 $in^2$) applied to the application site. STAY C50 was extracted from the tape strips by sonicating the samples in water for 30 minutes and analyzing the samples by HPLC. The tape strips showed delivery of STAY-C50 to the 10th layer of stratum corneum (FIG. 9).

Method: The distribution of lysozyme within the stratum corneum was assessed by serial tape stripping of the skin to which a lysozyme-calcium phosphate particle formulation was applied. An application site on the forearm of a human subject was marked and 200 μl of the formulation spread by spatula. The site was allowed to dry for 10 minutes and then followed by ten pre-weighed tape stripping using strips of (3 $in^2$) applied to the application site. Lysozyme was extracted from the tape strips by sonicating the samples in water for 30 minutes and analyzing the samples by HPLC. Lysozyme was detected to a depth of 6 tape strips (FIG. 10).

5. Controlled Slow Release of Active Agents by Franz Cell

Purpose: The purpose of this study was to detect riboflavin from riboflavin attached to calcium phosphate particles.

Methods:

Circular 6 $cm^2$ discs of full-thickness pig skin were cut from a larger abdominal specimen. Fat was removed from the dermis-side by scissors and the skin was stored at −20° C. until use. The skin was affixed between the two compartments of the glass diffusion cell (Laboratory Glass Apparatus, Model #LG-1084-LPCT). This allowed an exposed skin area of 5 $cm^2$ over a receptor compartment volume of 4.5 ml. The diffusion cell was maintained at 37° C.

Penetration Conditions

Topical application intervals were 8 and 16 hrs. The cells were covered with parafilm and shielded from light by aluminum wrap. A receptor fluid of phosphate buffered saline (PBS) was spun at 60 rpm.

Applied Formulations

Riboflavin monophosphate-calcium phosphate particles were prepared to deliver 0.35-1.15 mg riboflavin (20-38% suspensions).

Riboflavin monophosphate in PBS was prepared at 1.5 mg/mL to deliver 0.3-0.45 mg riboflavin.

Formulations were applied by pipette in volumes of 50-100 μl. Riboflavin-calcium phosphate complex applications were allowed to air dry and then equal volume of 0.5 M sodium acetate buffer was pipetted onto the application site. Controls consisted of equivalent applications of riboflavin without calcium phosphate particles.

Sample Collection

The skin surface, while still retained in the diffusion cell, was washed twice with 1 mL PBS each time. The skin was removed from diffusion cell and dried and analyzed.

Sample Analysis

Washes and Receptor fluid: The approximate volume of the fluids was determined. The samples were spun at 10,000 rpm for 30 seconds and the calcium phosphate particles separated, dried and weighed. The supernatant was then removed and analyzed by UV spectrometer. If the UV absorbance was saturated (over >2.0), the samples were diluted with water. The UV absorbance value at 370 nm was recorded.

Skin: The skin was minced and mixed with 5 ml of 10% trichloracetic acid solution. The sample was sonicated with ultrasonic apparatus at 50° C. for 1 hour. The sample was centrifuged at 10,000 rpm for 10 minutes, the supernatant removed and analyze by UV spectrometer. If the UV absorbance was saturated (over >2.0), samples were diluted with water. The maximum UV absorbance value at 370 nm was recorded.

Results

Figure 11:
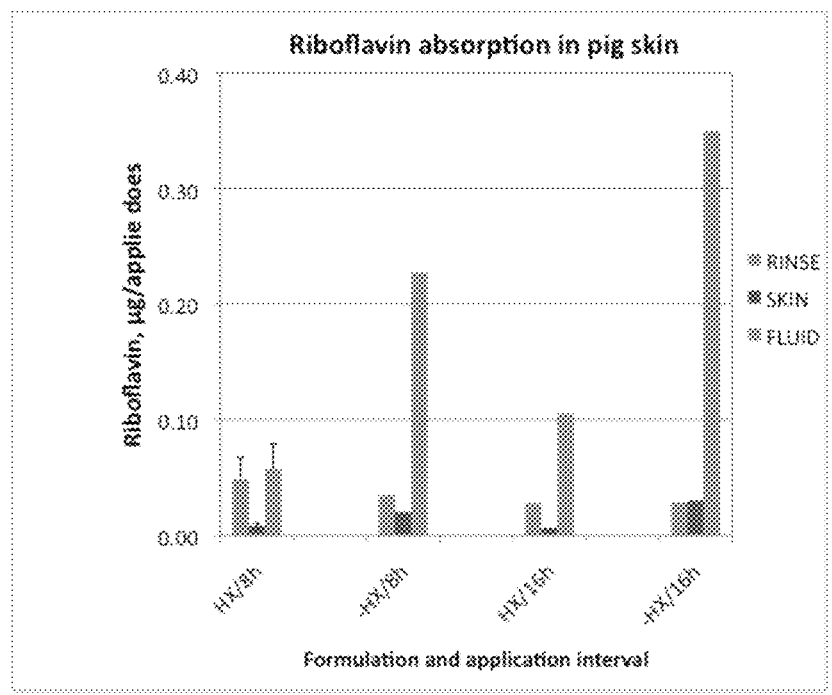
FIG. 11 shows Franz cell transdermal delivery of a riboflavin monophosphate active agent with and without calcium phosphate particles.

As detected by the appearance of riboflavin metabolite in the receptor fluid after 8 and 16 hours, riboflavin penetrated through skin from both the aqueous solution and from calcium phosphate particle complex. The calcium phosphate particle complex caused a slower release of the active. The results are shown graphically in FIG. 11.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of delivering an active agent to a subject, the method comprising:

applying a composition comprising:

spherical nanoporous calcium phosphate particles, wherein the particles are complexed with an active agent and 60 % or more of the particles in the composition have a diameter ranging from 0.1 μm to 2 μm;

to a topical region of the subject to deliver the active agent to the subject.

2. The method according to claim 1, wherein the particles have a porosity ranging from 30 % to 85 % as determined by ASTM D 4284-88.

3. The method according to claim 2, wherein the particles have a pore size ranging from 2 nm to 100 nm.

4. The method according to claim 1, wherein the amount of active agent complexed with the particles ranges from 0.01 mg to 300 mg active agent per gram of particles.

5. The method according to claim 1, wherein the topical region is a mucosal location.

6. The method according to claim 1, wherein the topical region is a keratinized skin surface.

7. The method according to claim 6, wherein the method is a method of delivering the active agent at least into the stratum corneum of the subject.

8. The method according to claim 6, wherein the method is a method of delivering the active agent into the deep stratum corneum of the subject.

9. The method according to claim 6, wherein the method is a method of delivering the active agent through the stratum corneum.

10. The method according to claim 6, wherein the method is a method of delivering the active agent into the dermis of the subject.

11. The method according to claim 6, wherein the method is a method of systemically delivering the active agent to the subject.

12. The method according to claim 1, wherein 75% or more of the particles in the composition have a diameter ranging from 0.1 μm to 2 μm.

* * * * *